(12) United States Patent
Arnett et al.

(10) Patent No.: US 7,144,383 B2
(45) Date of Patent: *Dec. 5, 2006

(54) SURGICAL/MEDICAL IRRIGATING HANDPIECE WITH VARIABLE SPEED PUMP, INTEGRATED SUCTION AND BATTERY PACK

(75) Inventors: Jeffery D. Arnett, Kalamazoo, MI (US); Nicholas V Gately, Portage, MI (US); David H. Grulke, Battle Creek, MI (US); Ruth A. Hilsbos, Saline, MI (US); James L Sertic, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/838,890

(22) Filed: May 4, 2004

(65) Prior Publication Data

US 2004/0210186 A1  Oct. 21, 2004

Related U.S. Application Data

(63) Continuation of application No. 09/460,705, filed on Dec. 14, 1999, now Pat. No. 6,746,419, which is a continuation of application No. 09/009,657, filed on Jan. 20, 1998, now Pat. No. 6,022,329, which is a continuation of application No. 08/559,133, filed on Nov. 17, 1995, now Pat. No. 5,718,668, which is a continuation of application No. 08/049,144, filed on Apr. 19, 1993, now Pat. No. 5,470,305.

(51) Int. Cl.
*A61M 3/00* (2006.01)
*A61M 3/02* (2006.01)

(52) U.S. Cl. .................. 604/35; 604/153; 604/246; 604/902; 601/155; 601/161

(58) Field of Classification Search ................ 601/155, 601/154, 160–165; 604/153, 246, 631, 902, 604/19, 28, 30–35, 119; 239/93, 320, 239, 239/263.1, 526

See application file for complete search history.

(56) References Cited

U.S. PATENT DOCUMENTS

| | | |
|---|---|---|
| 509,220 A | 11/1893 | Gustafson |
| 602,666 A | 4/1898 | Schroeder |
| 738,503 A | 9/1903 | Waters |
| 790,353 A | 5/1905 | Estlingen |
| 1,317,851 A | 10/1919 | Arnett |
| 1,503,279 A | 7/1924 | Nixon |
| 1,538,007 A | 5/1925 | Schellin |
| 1,846,596 A | 2/1932 | Hertzberg |

(Continued)

FOREIGN PATENT DOCUMENTS

DE  24 16 099  4/1975

(Continued)

OTHER PUBLICATIONS

Copy of Ethicon, Pfizer/Valley Lab and Bard/Davol photos (10 photos) Jun. 25, 1993.

(Continued)

*Primary Examiner*—Danton DeMille

(57) ABSTRACT

A medical/surgical irrigating handpiece with both a discharge line through which fluid is applied to the site and a suction line through which the discharge fluid is drawn away. The handpiece has a variable speed pulse pump. A single, variable-speed motor actuates the pump to regulate the pumping rate. Power to actuate the motor comes from a battery pack that remote to the handpiece. A control mechanism attached to the handpiece regulates the energization signal applied to the motor so as to regulate motor speed.

46 Claims, 17 Drawing Sheets

U.S. PATENT DOCUMENTS

| | | |
|---|---|---|
| 2,012,886 A | 8/1935 | Lowry |
| 2,112,629 A | 3/1938 | Lloyd |
| 2,139,653 A | 12/1938 | Belfrage |
| 2,197,995 A | 4/1940 | Crowley |
| 2,243,285 A | 5/1941 | Pope |
| 2,243,299 A | 5/1941 | Travers |
| 2,494,088 A | 1/1950 | Dulity |
| 2,531,793 A | 11/1950 | Sulek |
| 2,595,491 A | 5/1952 | Schweikert |
| 2,634,885 A | 4/1953 | North |
| 2,662,485 A | 12/1953 | Ilfrey |
| 2,684,049 A | 7/1954 | Hollis |
| 2,727,678 A | 12/1955 | Henderson |
| 2,733,713 A | 2/1956 | Kabnick |
| 2,781,154 A | 2/1957 | Meredith |
| 2,802,466 A | 8/1957 | Thomas |
| 2,847,007 A | 8/1958 | Fox |
| 2,874,696 A | 2/1959 | Bried |
| 2,908,273 A | 10/1959 | Huston |
| 2,993,654 A | 7/1961 | Norton |
| 3,001,288 A | 9/1961 | Freedman |
| 3,014,623 A | 12/1961 | Horn et al. |
| 3,039,272 A | 6/1962 | Frick |
| 3,044,465 A | 7/1962 | Anderson et al. |
| 3,048,121 A | 8/1962 | Sheesley |
| 3,065,749 A | 11/1962 | Brass |
| 3,070,089 A | 12/1962 | Dick |
| 3,135,259 A | 6/1964 | Evans |
| 3,208,145 A | 9/1965 | Turner |
| 3,227,158 A | 1/1966 | Mattingly |
| 3,237,306 A | 3/1966 | Staunt |
| 3,263,618 A | 8/1966 | Carpenter |
| 3,295,371 A | 1/1967 | Smith |
| 3,316,845 A | 5/1967 | Schumann |
| 3,353,537 A | 11/1967 | Knox et al. |
| 3,359,909 A | 12/1967 | Johnson et al. |
| 3,393,673 A | 7/1968 | Mattingly |
| 3,416,567 A | 12/1968 | VonDardel et al. |
| 3,425,410 A | 2/1969 | Cammack |
| 3,426,743 A | 2/1969 | Chesnut et al. |
| 3,448,766 A | 6/1969 | Schuele |
| 3,452,746 A | 7/1969 | Shanhouse |
| 3,484,121 A | 12/1969 | Quinton |
| 3,508,546 A | 4/1970 | Rogers et al. |
| 3,515,130 A | 6/1970 | Tsujino |
| 3,561,433 A | 2/1971 | Kovach |
| 3,601,164 A | 8/1971 | Bruce |
| 3,605,556 A | 9/1971 | Erdmann |
| 3,635,607 A | 1/1972 | Grise |
| 3,653,377 A | 4/1972 | Rebold |
| 3,702,141 A | 11/1972 | Wetterhorn |
| 3,703,170 A * | 11/1972 | Ryckman, Jr. .............. 601/162 |
| 3,713,533 A | 1/1973 | Reimels |
| 3,731,411 A | 5/1973 | Barber et al. |
| 3,731,676 A | 5/1973 | Rebold |
| 3,749,090 A | 7/1973 | Stewart |
| 3,762,411 A | 10/1973 | Lloyd et al. |
| 3,765,802 A | 10/1973 | Leitermann et al. |
| 3,768,472 A | 10/1973 | Hodosh et al. |
| 3,771,522 A | 11/1973 | Waysilk et al. |
| 3,784,235 A | 1/1974 | Kessler et al. |
| 3,794,031 A | 2/1974 | Bloom |
| 3,853,245 A | 12/1974 | Branch |
| 3,861,383 A | 1/1975 | Kovach |
| 3,883,074 A | 5/1975 | Lambert |
| 3,889,675 A | 6/1975 | Stewart |
| 3,895,741 A | 7/1975 | Nugent |
| 3,949,753 A | 4/1976 | Dockhorn |
| 3,965,934 A | 6/1976 | Rosenberg |
| 3,982,540 A | 9/1976 | Ross |
| 3,986,266 A | 10/1976 | Vellender |
| 3,993,054 A | 11/1976 | Newman |
| 4,007,739 A | 2/1977 | Bron et al. |
| 4,030,495 A | 6/1977 | Virag |
| 4,030,498 A | 6/1977 | Tompkins |
| 4,061,142 A | 12/1977 | Tuttle |
| 4,099,527 A | 7/1978 | Howell |
| 4,111,391 A | 9/1978 | Pilolla |
| 4,123,091 A | 10/1978 | Cosentino et al. |
| 4,205,676 A | 6/1980 | Humphrey et al. |
| 4,215,476 A | 8/1980 | Armstrong |
| 4,236,889 A * | 12/1980 | Wright ....................... 433/86 |
| 4,248,589 A | 2/1981 | Lewis |
| 4,250,872 A | 2/1981 | Tamari |
| 4,257,416 A | 3/1981 | Prager |
| 4,267,947 A | 5/1981 | Wasserstrom |
| 4,275,726 A | 6/1981 | Schael |
| 4,276,023 A | 6/1981 | Phillips et al. |
| 4,278,078 A | 7/1981 | Smith |
| 4,282,867 A | 8/1981 | Du Toit |
| 4,289,158 A | 9/1981 | Nehring |
| 4,290,454 A | 9/1981 | Shetler |
| 4,294,251 A | 10/1981 | Greenwald et al. |
| 4,300,748 A | 11/1981 | Kreeley |
| 4,301,971 A * | 11/1981 | Cornelius et al. ........... 239/351 |
| 4,313,699 A | 2/1982 | Steele |
| 4,314,560 A | 2/1982 | Helfgott et al. |
| 4,346,869 A | 8/1982 | MacNeill |
| 4,350,477 A | 9/1982 | Mazal |
| 4,395,205 A | 7/1983 | McCullough |
| 4,424,010 A | 1/1984 | McCullough |
| 4,424,055 A | 1/1984 | Herman |
| 4,428,345 A | 1/1984 | Bertsch et al. |
| 4,428,748 A | 1/1984 | Peyman et al. |
| 4,436,495 A | 3/1984 | McCullough |
| 4,445,819 A | 5/1984 | Walling |
| 4,449,827 A | 5/1984 | Karkiewicz |
| 4,451,069 A | 5/1984 | Melone |
| 4,460,358 A | 7/1984 | Somerville et al. |
| 4,468,221 A | 8/1984 | Mayfield |
| 4,472,120 A | 9/1984 | McCullough |
| 4,482,345 A | 11/1984 | Chow et al. |
| 4,484,769 A | 11/1984 | Lacey |
| 4,489,750 A | 12/1984 | Nehring |
| 4,493,694 A | 1/1985 | Wuchinich |
| 4,502,502 A | 3/1985 | Krug |
| 4,508,532 A | 4/1985 | Drews et al. |
| 4,509,507 A | 4/1985 | Yabe |
| 4,512,066 A | 4/1985 | McCullough |
| 4,515,532 A | 5/1985 | Walling |
| 4,519,385 A | 5/1985 | Atkinson et al. |
| 4,526,573 A | 7/1985 | Lester et al. |
| 4,534,758 A | 8/1985 | Akers et al. |
| 4,535,773 A | 8/1985 | Yoon |
| 4,537,182 A | 8/1985 | Otani |
| 4,537,209 A | 8/1985 | Sasa |
| D281,535 S | 11/1985 | Atkinson et al. |
| 4,552,130 A | 11/1985 | Kinoshita |
| 4,553,957 A | 11/1985 | Williams et al. |
| 4,561,431 A | 12/1985 | Atkinson |
| 4,561,856 A | 12/1985 | Cochran |
| 4,580,816 A | 4/1986 | Campbell et al. |
| 4,583,531 A | 4/1986 | Mattchen |
| 4,592,749 A | 6/1986 | Ebling et al. |
| 4,596,558 A | 6/1986 | Smith et al. |
| 4,601,710 A | 7/1986 | Moll |
| 4,604,089 A | 8/1986 | Santangelo et al. |
| 4,621,770 A | 11/1986 | Sayen |
| 4,634,420 A | 1/1987 | Spinosa et al. |
| 4,635,621 A | 1/1987 | Atkinson |
| 4,647,738 A | 3/1987 | Diamond |
| 4,655,197 A | 4/1987 | Atkinson |
| 4,655,744 A | 4/1987 | Thistle et al. |
| 4,655,752 A | 4/1987 | Honkanen et al. |

| | | |
|---|---|---|
| 4,655,754 A | 4/1987 | Richmond |
| 4,655,765 A | 4/1987 | Swift |
| 4,662,829 A | 5/1987 | Nehring |
| 4,667,655 A | 5/1987 | Ogiu et al. |
| 4,692,140 A | 9/1987 | Olson |
| 4,696,669 A | 9/1987 | Menhusen |
| 4,705,500 A | 11/1987 | Reimels et al. |
| 4,741,678 A | 5/1988 | Nehring |
| 4,748,970 A | 6/1988 | Nakajima |
| 4,759,349 A | 7/1988 | Betz et al. |
| 4,764,165 A | 8/1988 | Reimels et al. |
| 4,765,165 A | 8/1988 | Reimels et al. |
| 4,765,588 A | 8/1988 | Atkinson |
| 4,776,840 A | 10/1988 | Freitas et al. |
| 4,799,481 A | 1/1989 | Transue et al. |
| 4,817,599 A | 4/1989 | Drews |
| 4,857,068 A | 8/1989 | Kahn |
| 4,872,837 A | 10/1989 | Issalene et al. |
| 4,892,469 A | 1/1990 | McCullough et al. |
| 4,911,621 A | 3/1990 | McCullough et al. |
| 4,925,450 A | 5/1990 | Imonti et al. |
| 4,927,340 A | 5/1990 | McCullough |
| 4,935,005 A | 6/1990 | Haines |
| 4,941,872 A | 7/1990 | Felix et al. |
| 4,957,483 A | 9/1990 | Gonser et al. |
| 4,978,282 A | 12/1990 | Fu et al. |
| 4,982,739 A | 1/1991 | Hemstreet et al. |
| 5,019,038 A | 5/1991 | Linden |
| 5,037,431 A | 8/1991 | Summers et al. |
| 5,046,486 A | 9/1991 | Grulke et al. |
| 5,049,071 A | 9/1991 | Davis et al. |
| 5,053,002 A | 10/1991 | Barlow |
| 5,054,947 A | 10/1991 | Frank et al. |
| 5,057,015 A | 10/1991 | Fleer |
| 5,098,387 A | 3/1992 | Wiest et al. |
| 5,098,405 A | 3/1992 | Peterson et al. |
| 5,100,058 A | 3/1992 | Wei |
| 5,120,305 A | 6/1992 | Boehringer et al. |
| 5,142,723 A | 9/1992 | Lustig |
| 5,147,292 A | 9/1992 | Kullas et al. |
| 5,170,779 A | 12/1992 | Ginsberg |
| 5,176,629 A | 1/1993 | Kullas et al. |
| 5,186,714 A | 2/1993 | Boudreault et al. |
| 5,188,591 A | 2/1993 | Dorsey, III |
| 5,195,958 A | 3/1993 | Phillips |
| 5,195,959 A | 3/1993 | Smith |
| 5,197,460 A | 3/1993 | Ito |
| 5,203,769 A | 4/1993 | Clement et al. |
| 5,224,929 A | 7/1993 | Remiszewski |
| 5,244,459 A | 9/1993 | Hill |
| 5,261,905 A | 11/1993 | Doresey, III |
| 5,269,750 A | 12/1993 | Grulke et al. |
| 5,281,214 A | 1/1994 | Wilkins et al. |
| 5,295,956 A | 3/1994 | Bales et al. |
| 5,303,735 A | 4/1994 | Cerola et al. |
| 5,305,735 A | 4/1994 | Welden |
| 5,322,503 A | 6/1994 | Desai |
| 5,322,506 A | 6/1994 | Kullas |
| 5,333,603 A | 8/1994 | Schuman |
| 5,334,140 A | 8/1994 | Phillips |
| 5,336,238 A | 8/1994 | Holmes et al. |
| 5,348,555 A | 9/1994 | Zinmanti |
| 5,380,277 A | 1/1995 | Phillips |
| 5,388,612 A | 2/1995 | Cerola et al. |
| 5,391,145 A | 2/1995 | Dorsey |
| D358,200 S | 5/1995 | Cerola |
| 5,431,676 A | 7/1995 | Dubrul et al. |
| 5,447,494 A | 9/1995 | Dorsey, III |
| 5,449,357 A | 9/1995 | Zinmanti |
| 5,470,305 A | 11/1995 | Arnett et al. |
| 5,484,402 A | 1/1996 | Saravia et al. |
| 5,487,649 A | 1/1996 | Dorsey, III et al. |
| 5,514,089 A | 5/1996 | Walbrink et al. |
| 5,522,796 A | 6/1996 | Dorsey, III |
| 5,562,640 A | 10/1996 | McCabe et al. |
| 5,573,504 A | 11/1996 | Dorsey, III |
| 5,578,000 A | 11/1996 | Greff et al. |
| 5,586,977 A | 12/1996 | Dorsey, III |
| 5,607,391 A | 3/1997 | Klinger et al. |
| 5,609,573 A | 3/1997 | Sandock |
| D385,889 S | 11/1997 | Kullas et al. |
| 5,707,351 A | 1/1998 | Dorsey, III |
| 5,718,668 A | 2/1998 | Arnett et al. |
| 5,746,721 A | 5/1998 | Pasch et al. |
| 5,792,098 A | 8/1998 | Felix et al. |
| 5,792,108 A | 8/1998 | Felix et al. |
| 5,807,313 A | 9/1998 | Delk et al. |
| 5,810,770 A | 9/1998 | Chin et al. |
| 5,827,218 A | 10/1998 | Nguyen et al. |
| 5,924,448 A | 7/1999 | West |
| 5,941,851 A | 8/1999 | Coffey et al. |
| 6,022,329 A | 2/2000 | Arnett et al. |
| 6,059,754 A | 5/2000 | Pasch et al. |
| 6,095,772 A | 8/2000 | Ramey et al. |
| 6,099,494 A | 8/2000 | Henniges et al. |
| 6,106,494 A | 8/2000 | Saravia et al. |
| 6,156,004 A | 12/2000 | Tremaine et al. |
| 6,162,194 A | 12/2000 | Shipp |
| 6,176,847 B1 | 1/2001 | Humphreys, Jr. et al. |
| 6,179,807 B1 | 1/2001 | Henniges et al. |
| 6,200,292 B1 | 3/2001 | French et al. |
| 6,213,970 B1 | 4/2001 | Nelson et al. |
| 6,352,527 B1 | 3/2002 | Henniges et al. |
| 6,358,224 B1 | 3/2002 | Tims et al. |
| 6,371,934 B1 | 4/2002 | Jackson et al. |
| 6,394,996 B1 | 5/2002 | Lawrence et al. |
| 6,471,668 B1 | 10/2002 | Henniges et al. |
| 6,485,452 B1 | 11/2002 | French et al. |
| 6,623,445 B1 | 9/2003 | Nelson et al. |
| 6,626,827 B1 | 9/2003 | Felix et al. |
| 6,685,667 B1 | 2/2004 | Delk et al. |
| 2001/0025160 A1 | 9/2001 | Felix et al. |
| 2002/0082557 A1 | 6/2002 | Jackson et al. |

FOREIGN PATENT DOCUMENTS

| | | |
|---|---|---|
| EP | 0 258 901 | 3/1988 |
| FR | 1 325 670 | 3/1963 |
| GB | 1 264 138 | 2/1972 |
| GB | 2 063 674 A | 6/1981 |
| WO | WO81/01794 | 7/1981 |
| WO | WO81/02335 | 8/1981 |
| WO | WO85/03982 | 9/1985 |
| WO | WO86/04247 | 8/1986 |
| WO | WO91/12830 | 9/1991 |
| WO | WO92/21388 | 12/1992 |
| WO | WO93/17733 | 9/1993 |
| WO | WO94/13335 | 6/1994 |
| WO | WO94/19030 | 9/1994 |
| WO | WO94/23773 | 10/1994 |

OTHER PUBLICATIONS

KLI DeCherney Hysteroscopy Pump believed published before Apr. 19, 1993.

Marlow—Unique Products for Advanced Operative Laparoscopy 790—5M.

Select One—™ Minimal Access Surgery System, Introducing theVAC—™ Handcontrolled Suction Irrigation Instrument, ConMed Aspen Surgical Systems, Conmed Jul. 1992, 10M.

Select One—™ Minimal Access Surgery System, The Modular Instrument System for Surgical Endoscopy, SelectOne System by ConMed, Aspen Surgical Systems believed published before Apr. 19, 1993.

Davol—Endo-Flo™ Irrigator, Bard, Davol Inc.; instruction booklet # 041002-0, 9011R, Nov. 1990.

Count On US (Introducing Over 100 Precision Crafted Quality Endosurgery Instruments), Davis+Geck, 1993.

Essar® Suction Irrigator, Why do I need the *Essar* Suction Irrigator? Stewart Research, Inc. believed published before Apr. 19, 1993.

"Simultaneous pulsatile lavage and/or irrigation with suction . . . ", Pulsatile Lavage Debridement System, brochure No. 82-010-5150-0146/2.5M CISS Zimmer, Inc., Snyder Labs Inc, 1982.

Nezhat-Dorsey™ Hydro-Dissection™ Information Booklet Installation/Operating Instructions for "Quick-Disconnect" Probe Tips (2 sheets) believed published before Apr. 19, 1993.

Suction/Irrigator Is No Longer An Issue, Hydro-Dissection System, 556529 PP ICM Jul. 1992, Karl Stroz Gmbh & Co. Tuttlengen, West Germany.

A Fully Integrated Laparoscopic Irrigation and Instrumentation System, Cabot Medical, Langhorne, PA Apr. 1992, 10M, L/T (4 sheets).

Advances In Pelviscopy, The Irrigation Pump System, Cabot Medical, Langhorne, PA Apr. 1990 (3 sheets).

InteliJET™, Fluid Management System User' Manual, Smith & Nephew Dyonics Inc., copyright 1992, PN1060170.

Davol, Arthro-Flo®, Instructions For Use, 038657-0 901R C.R. Bard, Inc. Cranston RI, Jan. 1990.

Davol, Arthro-Flo High-Flo Irrigator, Bard, OP-AF0015000 Aug. 1992 5M C.R. Bard Inc. Cranston, RI.

3M Fluid Control System, For Precise Control of all Arthroscopic Procedures, 70-2008-5458-9, 1992 3M.

Davol, Instructions for Use, Simpulse—™ Suction/Irrigator, BARD, 034089-0 (2 sheets) Jan. 1985.

"Introducing the multi-functional instrument for virtually every laparoscopic case", USSC, Auto Suture Company, Copyright 1992, 556529 pp. 10M Jul. 1992.

Davol's Answers to Plaintiff's First Set of Interrogatories dated Jan. 7, 1996.

Davol's Supplemental Answers to Plaintiff's First Set of Interrogatories dated Feb. 14, 1997.

Deposition of Roger E. Darois, pp. 1-177, with index pp. 1-19 and correction and signature papers 1-3, dated May 7, 1997.

Rule 26(a) (2) Expert Report of Dr. Harrith M: Hasson Relating to Davol's Defenses to Stryker's Infringement Claims Under the '402 Patent dated Oct. 29, 1997 including Exhibits A-D.

Rule 26 (a) (2) Expert Report of Roger E. Daris Relating to Davol's Defenses to Styrker's Infringment Claims Under the '402 Patent dated Oct. 30, 1997 including exhibits A-D.

Rule 26 (a) (2) Rebuttal Expert Report of Dr. Harrith M. Hasson, M.D. Relating to Stryker's Infringement of United States Patent No. 5 391 145 and United States Patent No. 5 586 977, dated Dec. 8, 1997.

Deposition of Harrith M. Hasson, pp.1-281 with index pages 1-32 dated Feb. 13, 1998.

Davol's Supplemental Answers to Plaintiff's First Set of Interrogatories dated Feb. 14, 1997.

Ruling on Claim Construction Disputes dated Apr. 24, 1998.

Trial-vol. IV. IV, Nov. 17, 1998: (Hope-Cross; Darois-direct, voir dire, Cross) multi-channel fiber-optic rotary multipage 35-43 (actual pp. 524-785).

Trial-vol. V, Nov. 18, 1998 (Darois-direct) multipage 623-785; actual pp. 3-44.

Memorandum Opinion and Order Denying Motion for Judgment as a Matter of Law dated May 26, 1999.

Arthur D. Little (Tsals) Dec. 8, 1992 letter to Davol.

Bard (Brad Cilley) Oct. 16, 1992 fax to John Skreenock.

Arthur D. Little (Tsals) Nov. 12, 1992 fax to John Skreenock (Davol).

Arthur D. Little (Tsals) Dec. 17, 1992 letter to John Skreenock.

Arthur D. Little (Tsals) Jan. 28, 1993 letter to John Skreenock.

Saline Pump Development Program, Davol Inc., Jan. 18, 1993, Cambridge, MA.

Teltech Nov. 2, 1992 search for John Skreenock re Scroll Pumps.

Arthur D. Little (Sword) Sep. 8, 1992 letter to Albert Solis.

Davol (Silva) Jan. 4, 1993 letter to Arthur D. Little.

Saline Scroll Pump Development Program.

Scroll Technology in Medical Products.

\* cited by examiner

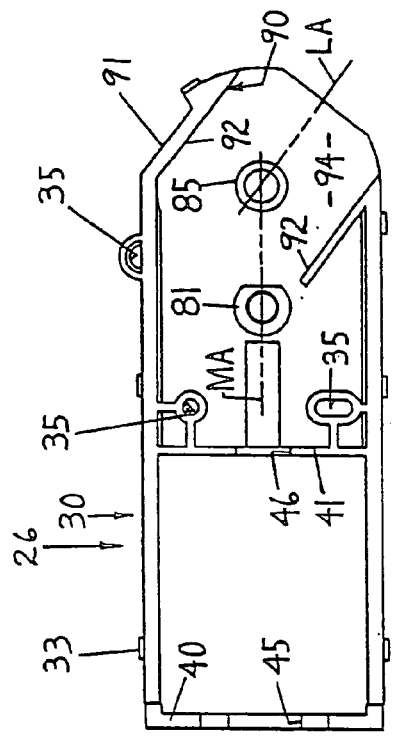
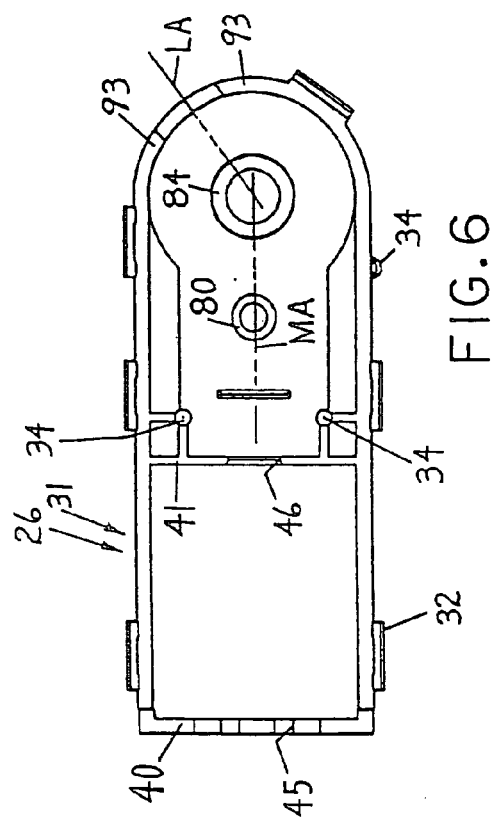
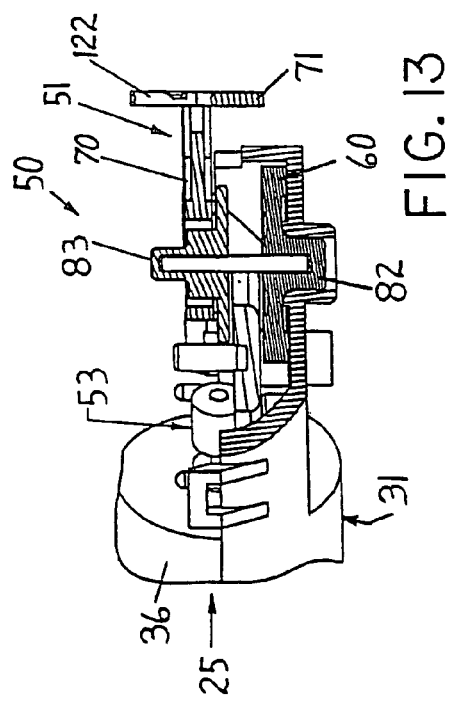
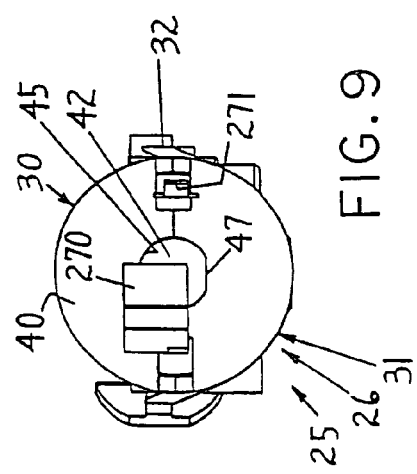

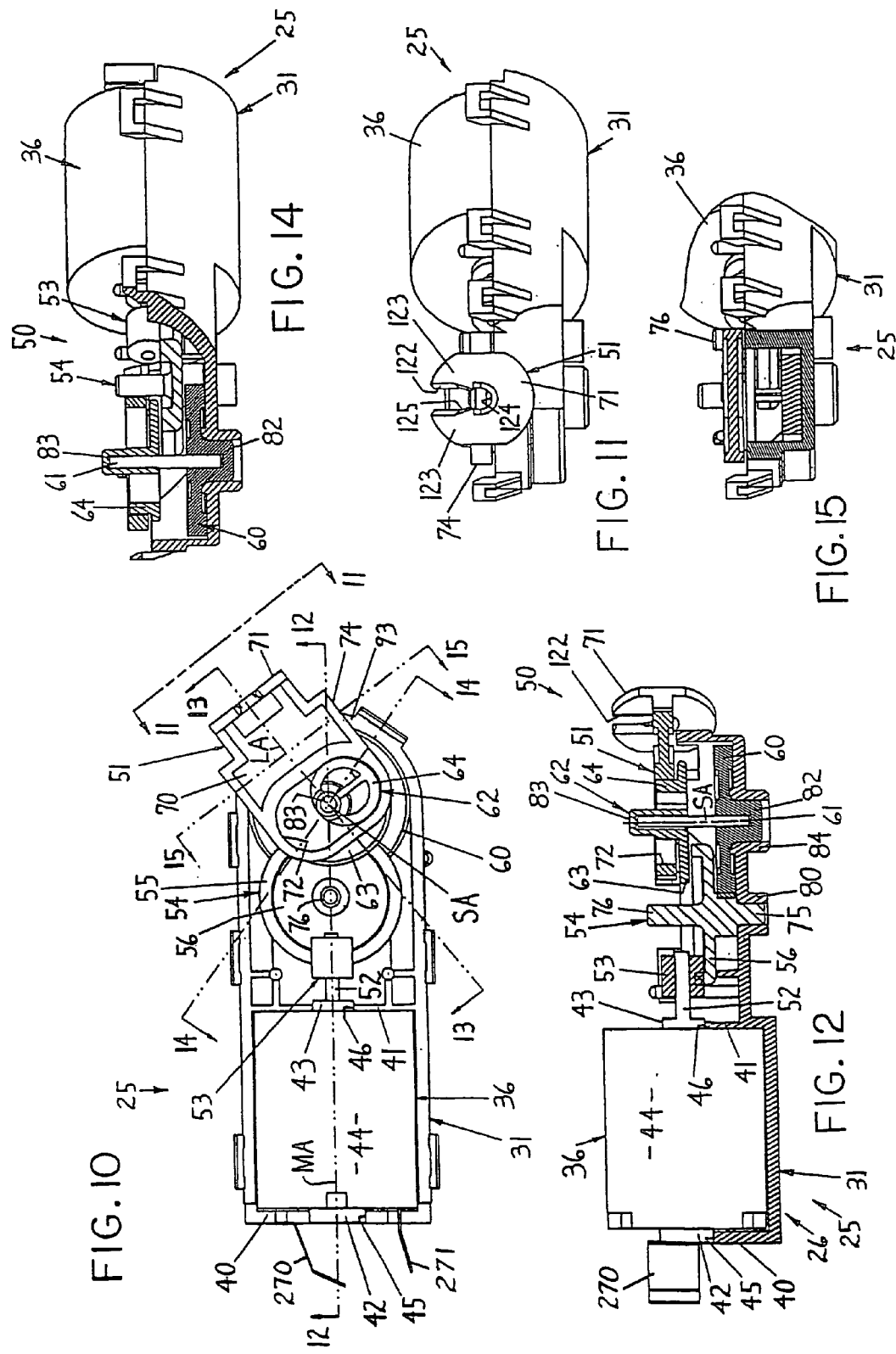

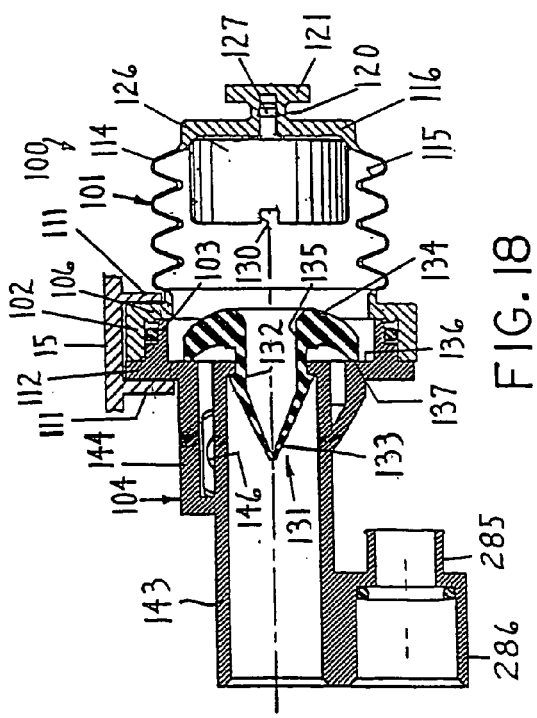

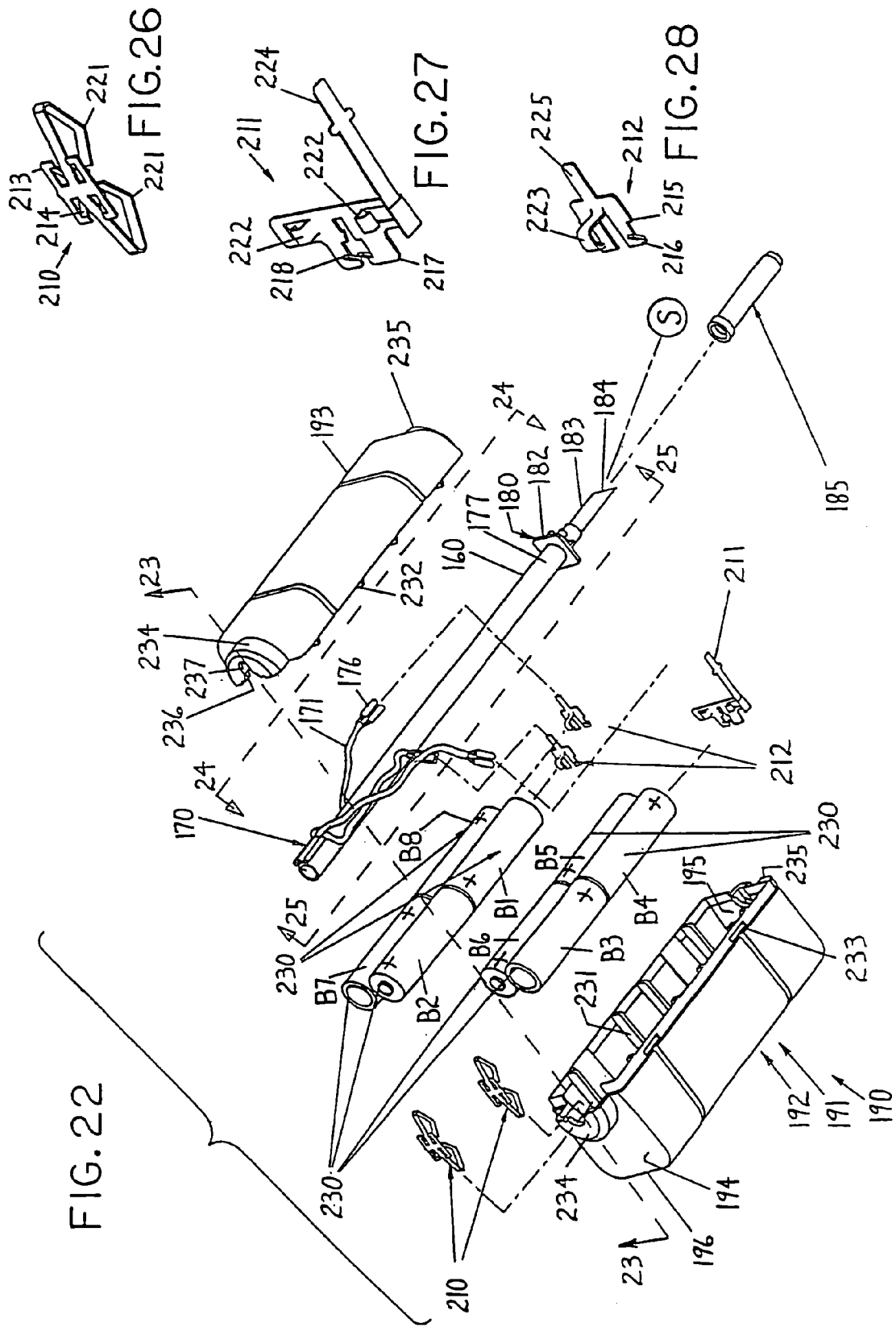

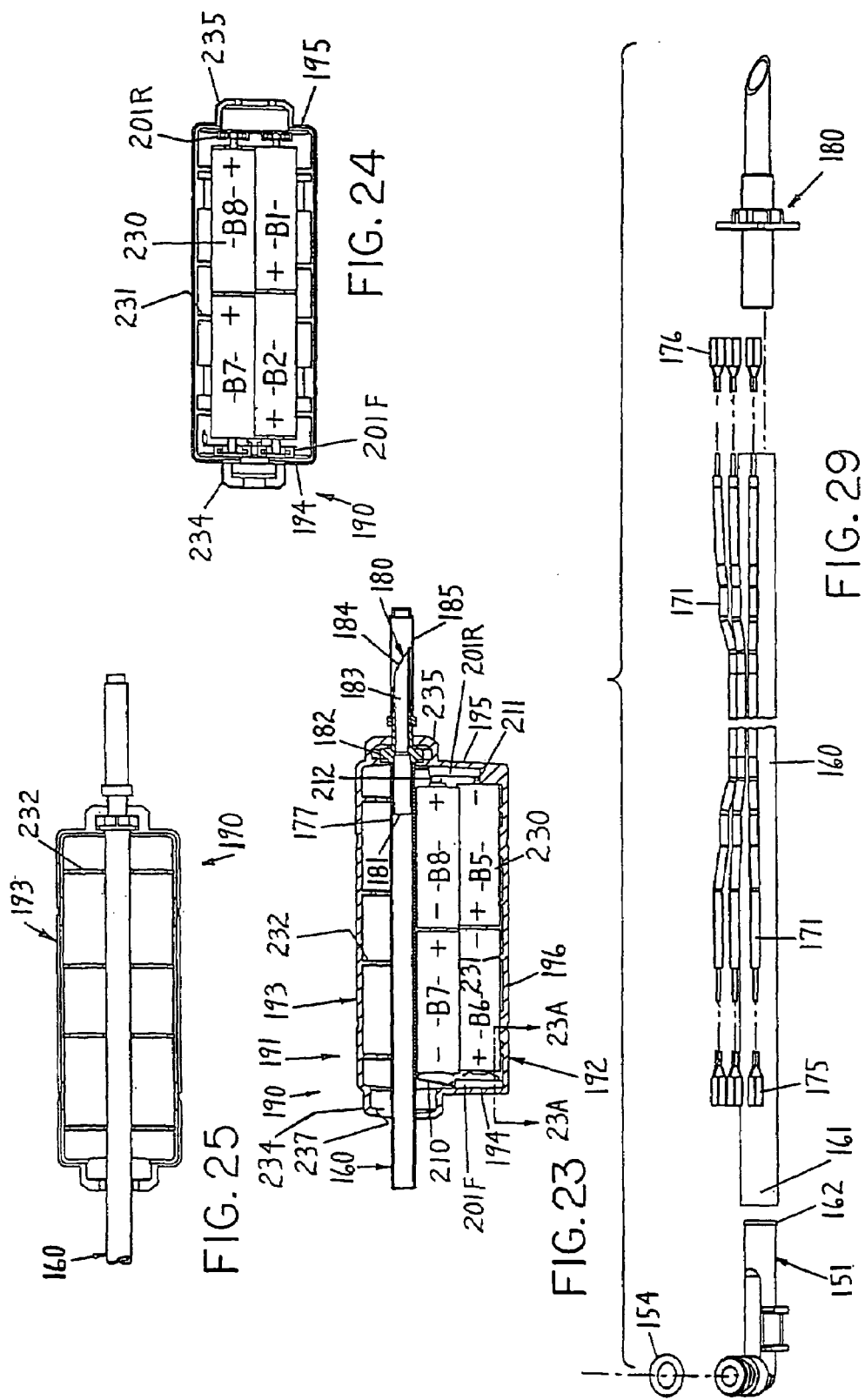

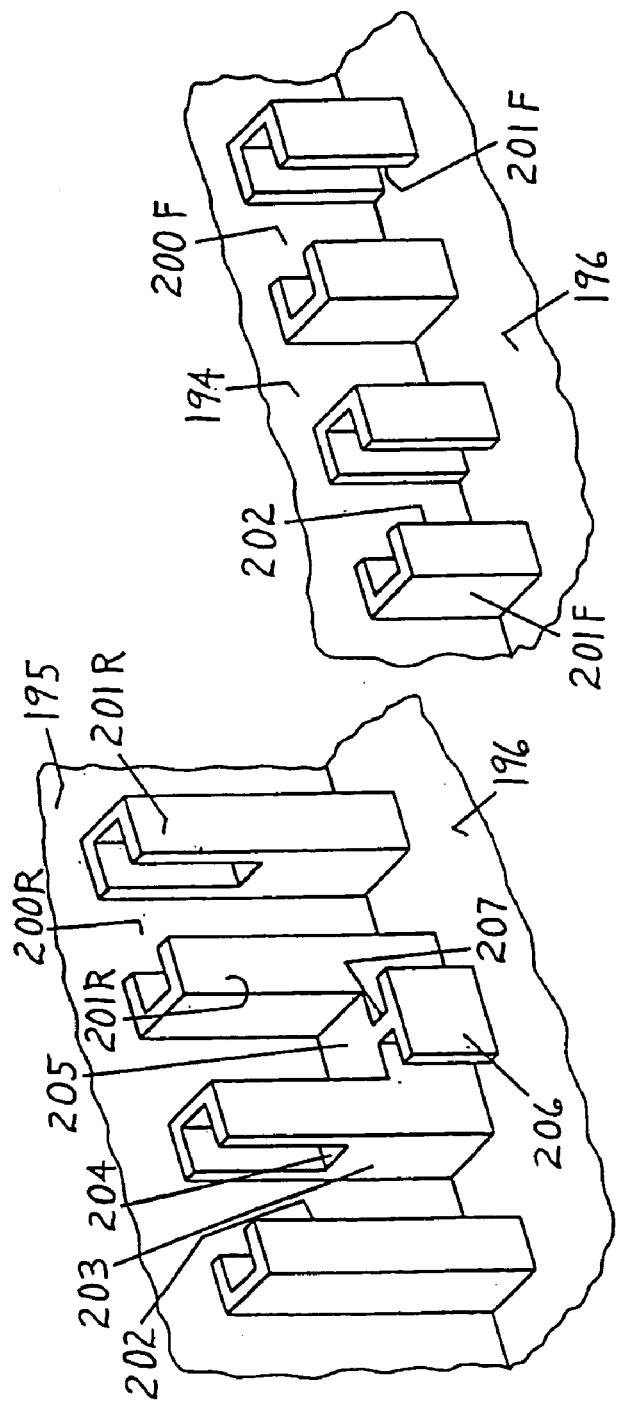

US 7,144,383 B2

SURGICAL/MEDICAL IRRIGATING HANDPIECE WITH VARIABLE SPEED PUMP, INTEGRATED SUCTION AND BATTERY PACK

This is a continuation of Ser. No. 09/460,705, filed Dec. 14, 1999, now U.S. Pat. No. 6,746,419, which is a continuation of Ser. No. 09/009,657, filed Jan. 20, 1998, now U.S. Pat. No. 6,022,329, issued Feb. 8, 2000 which is a continuation of Ser. No. 08/559,133, filed Nov. 17, 1995, now U.S. Pat. No. 5,718,668, issued Feb. 17, 1998 which is a continuation of Ser. No. 08/049,144, filed Apr. 19, 1993, now U.S. Pat. No. 5,470,305.

FIELD OF THE INVENTION

This invention relates to a surgical irrigation with a built in pulsing pump.

BACKGROUND OF THE INVENTION

Grulke et al U.S. Pat. No. 5,046,486, assigned to the Assignee of the present invention, discloses a surgical pulsed irrigation handpiece which produces a pulsed irrigation liquid output capable of loosening and floating debris at a surgical site for subsequent removal (as by suction). This prior pulsed irrigation handpiece has been on the market for several years and has proved generally effective for its intended use and hence has been popular in the surgical community.

However, in a continuing effort to improve on existing devices of this general kind, the present invention has been developed. As compared to the above-mentioned prior device, a pulsed irrigation handpiece embodying the present invention is producible at lower cost, produces sharper liquid pulse transients (particularly the pulse "off" transient), requires no connection to any operating room power source (e.g. compressed air) or to an external pump, and instead is self-contained, requires only external connection to a irrigation liquid source (e.g. conventional irrigation liquid bag), provides better suction (when suction is required), is more compact, and is conveniently shaped to be held either as a pistol or a wand (by the handle or barrel).

Other objects, purposes and advantages of the invention will be apparent to those acquainted with apparatus as general kind upon reading the following description and inspecting the accompanying drawings.

SUMMARY OF THE INVENTION

A pulsed irrigation handpiece comprises pulsed irrigation liquid outlet means for applying liquid pulses to a surgical site, pump means reciprocatingly drivable for pumping pulses of irrigation liquid through said outlet means, powered drive means for reciprocatingly driving said pump means and housing means containing said pump means and drive means.

BRIEF DESCRIPTION OF THE DRAWINGS

FIG. 4A is an enlarged fragment of FIG. 4 detailing the rearward portion of the handle.

FIG. 4B is an enlarged fragmentary pictorial view, taken from the front, of the electrical contact support posts seen in FIG. 4A.

FIG. 4C is an enlarged fragmentary exploded pictorial view of the electrical contacts, associated with the FIG. 4B posts and associated electrical conductors from the battery supply.

FIG. 6 is a sectional view substantially taken on the line 6—6 of FIG. 5, and provides a top view of the bottom drive unit shell part of FIG. 5 (the rightward one of FIG. 2) with the drive components removed to show the interior configuration of that shell part.

FIG. 7 is a sectional view substantially taken on the line 7—7 of FIG. 5, and provides a view similar to FIG. 6 but showing the interior configuration of the other drive unit shell part (the upper one in FIG. 5 and leftward one in FIG. 2).

FIG. 9 is an end elevational view of the drive unit, taken from the right end in FIGS. 2 and 3.

FIG. 10 is a sectional view substantially taken on the line 10—10 of FIG. 5 and showing the drive unit with one shell part (the left one in FIG. 2 and top one in FIG. 5) removed to show the motor and transmission.

FIG. 11 is an elevational view of the drive train substantially taken on the line 11—11 of FIG. 10.

FIG. 12 is a central cross-sectional view substantially taken on the line 12—12 of FIG. 10.

FIG. 13 is a fragmentary cross-sectional view substantially taken on the line 13—13 of FIG. 10.

FIG. 14 is a cross-sectional view substantially taken on the line 14—14 of FIG. 10.

FIG. 15 is a sectional view substantially taken on the line 15—15 of FIG. 10.

FIG. 18 is a central cross-sectional view of the pump unit of FIG. 17 taken substantially on the line 18—18 of FIG. 17.

FIG. 18A is a fragment of FIG. 18 showing the pump unit at the beginning of an intake stroke.

FIG. 18B is a fragment of FIG. 18 showing the pump nearing the end of an output pulse.

FIG. 19 is a fragmentary cross-sectional view showing the connection of the pump unit to the liquid supply hose.

FIG. 22 is an exploded pictorial view of the electric power supply unit of FIG. 20.

FIG. 23 is a central cross-sectional view taken substantially on the line 23—23 of FIG. 22.

FIG. 23A is an enlarged fragmentary pictorial view of the support structure for battery contacts at the forward (left in FIG. 23) end of the electric power supply casing.

FIG. 23B is an enlarged pictorial view similar to FIG. 23A but showing the support structure for battery contacts at the rearward (rightward in FIG. 23) end of the power supply casing.

FIG. 24 is a sectional view substantially taken on the line 24—24 of FIG. 22 and showing the electric power supply unit with its top cover removed.

FIG. 25 is a sectional view substantially taken on the line 25—25 of FIG. 22 and showing the underside of the cover of the power supply casing.

FIGS. 26, 27 and 28 are enlarged pictorial views of battery contacts of FIG. 22.

FIG. 29 is an enlarged fragmentary pictorial view of an embodiment of the liquid supply and electric wiring harness of the apparatus of FIGS. 2 and 20 but showing a modification in the attachment of the electrical and liquid handling components.

In the following detailed discussion the terms "up", "down", "right" and "left", and variations thereon, refer to structural elements in their positions in specified drawing figures.

DETAILED DESCRIPTION

Figure 1:
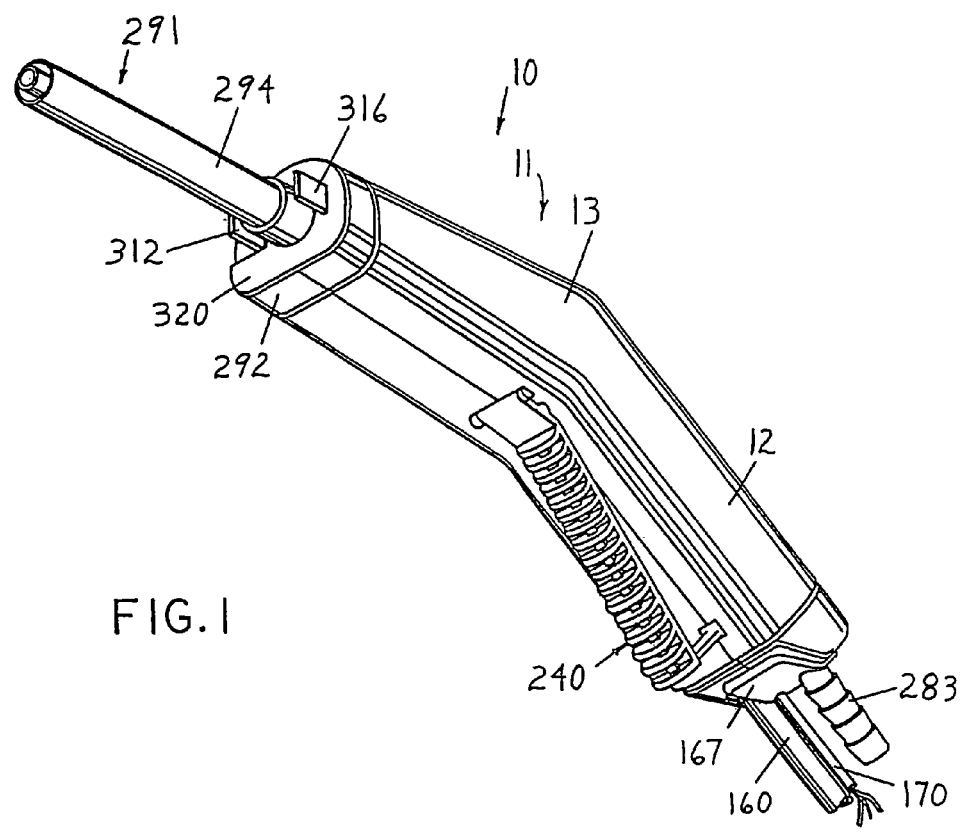
FIG. 1 is a pictorial view of a handpiece embodying the invention.

A pulsed irrigation handpiece 10 (FIGS. 1 and 2) embodying the invention comprises a hand-held housing 11 having a handle 12 and a barrel 13 which extends forward from the upper end of the handle 12 at about a 130° to 150° (here about 145°) angle thereto.

Figure 2:
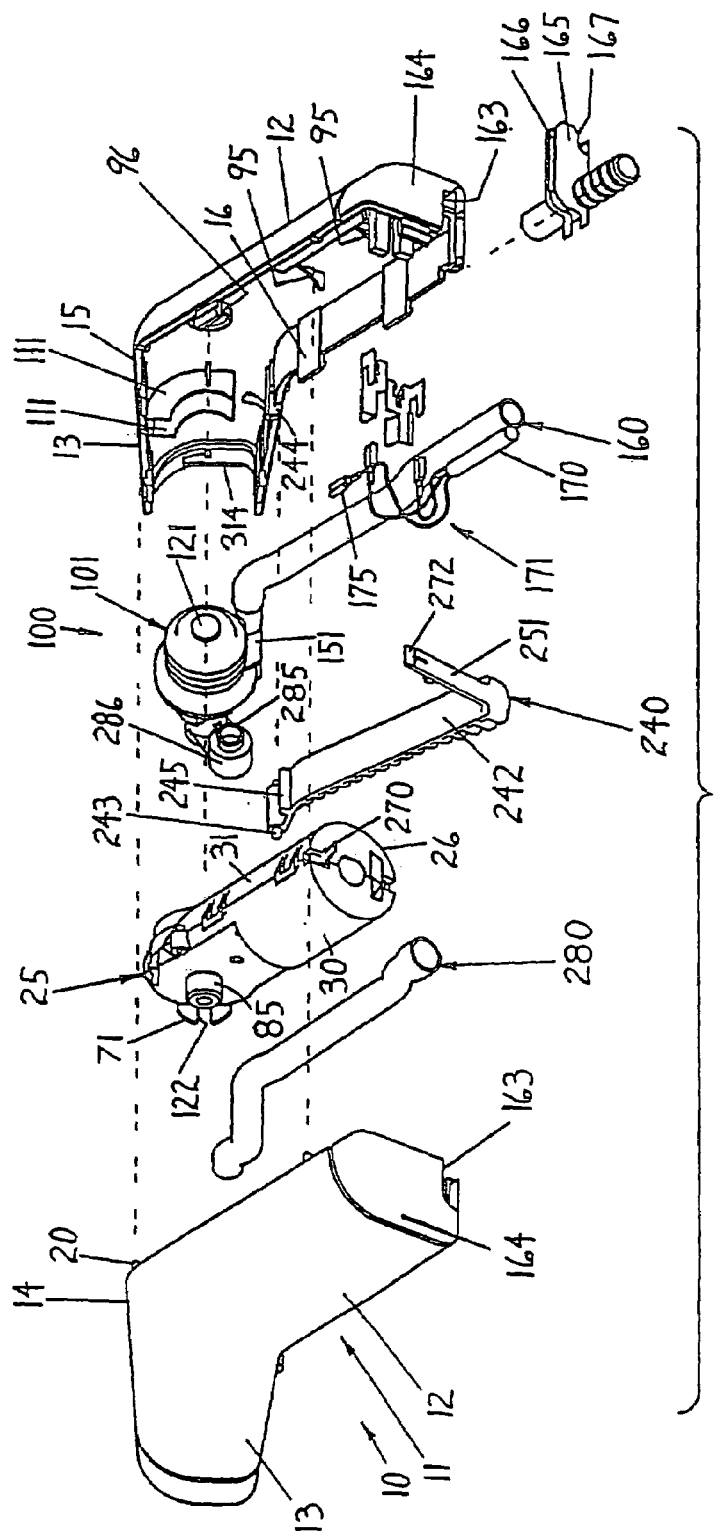
FIG. 2 is a laterally exploded pictorial view of the FIG. 1 handpiece.

The housing 11 is hollow and, for convenience in assembling the handpiece 10, is constructed as laterally opposed concave left and right housing parts 14 and 15 (FIG. 2). The housing parts 14 and 15 are preferably molded rigid plastic elements held together rigidly by any convenient means, here comprising undercut snap fit tabs 16 protruding from the top and bottom edges of the right housing part 15 to snap over an interior edge flange (not shown) on the top and bottom edge of the left housing part 14. If desired, precise registry together of the two housing parts can be assisted by laterally projecting pins 20 distributed along the edges of one housing part (here the left housing part 14) piloted in holes 21 (FIG. 4) in the opposed edges of the other housing part (here 15). Upon completion of assembly of the handpiece 10, the two housing parts 14 and 15 may be adhesively bonded together. The handpiece is intended to be a disposable item and therefore access to the interior of the housing for purposes of repair is not needed.

Drive Unit

Figure 4:
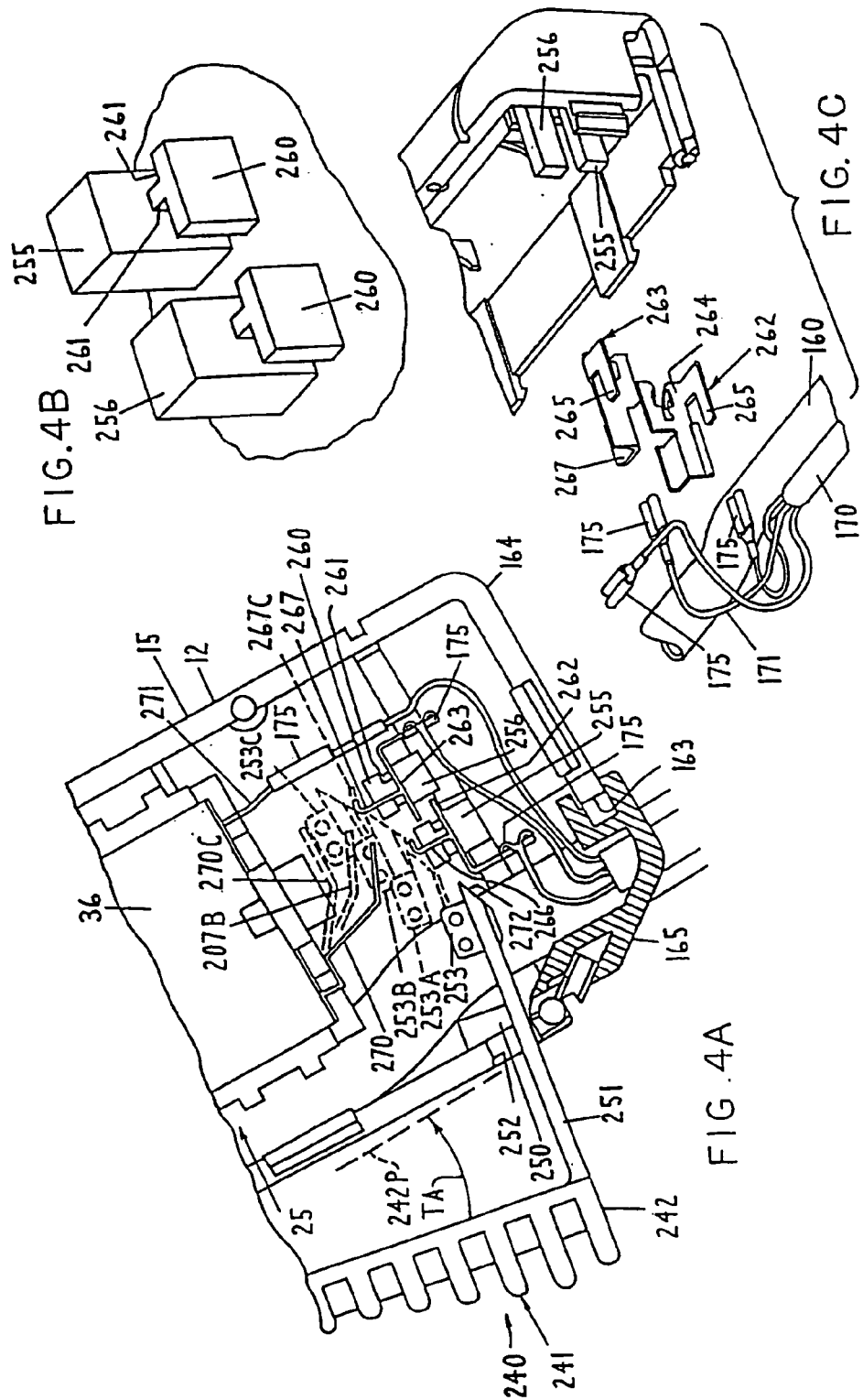
FIG. 4 is a view similar to FIG. 3 but with the suction hose removed, the left drive unit shell part removed and the drive unit exposed in central cross-section, such that FIG. 4 approximates a central cross-sectional view of the FIG. 1 handpiece.
Figure 5:
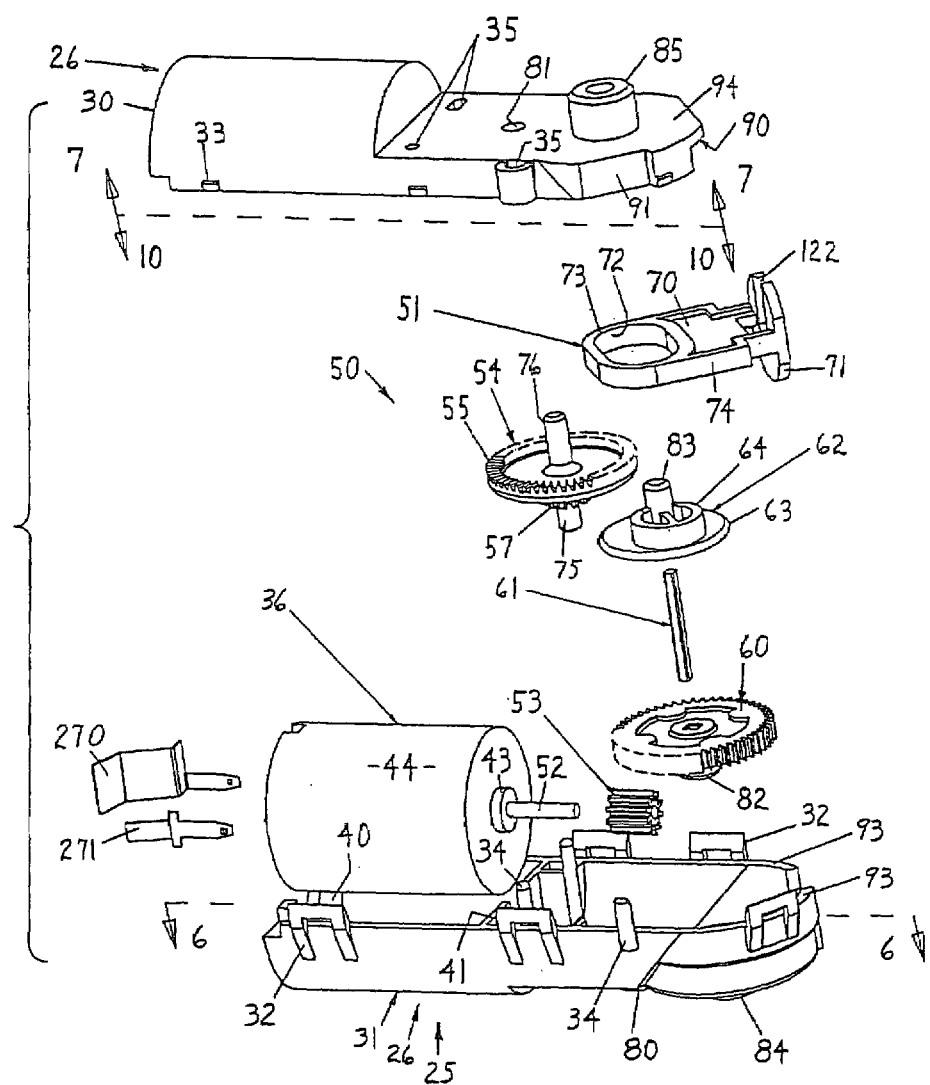
FIG. 5 is an enlarged, exploded, pictorial view of the drive unit of FIG. 2.

The drive unit 25 (FIGS. 2–15) is self contained in its own shell 26 (FIG. 2). For convenience in assembly, the shell 26 comprises two opposed concave shell parts 30 and 31 respectively disposed to the left and right in FIG. 2. The shell parts 30 and 31 are preferably of rigid molded plastics material. When the drive unit 25 has been assembled, as in FIGS. 2 and 9, the shell parts 30 and 31 are held fixedly together by any convenient means, here by resilient snap connection of generally U-shaped clips 32, molded in spaced relation along the perimeter edge of the shell part 31 which overlap the perimeter edge of the shell part 30 and snap over tabs 33 protruding therefrom, as seen in FIGS. 5–7. Precise location of the shell parts 30 and 31 with respect to each other is assisted by locator pins 34 fixedly protruding from the shell part 31 and holes 35 in the opposed portions of the shell part 30.

A single conventional DC energizable electric motor 36 (FIGS. 4 and 5) is snugly housed in the space between the left and right (FIG. 2) shell parts at the rear (left in FIGS. 5–7, 10 and 12) thereof. The motor 36 is snugly axially located between the rear end wall and a transverse internal bulkhead 41 of the shell 26 (FIGS. 5–7, 10 and 12). The rear end wall 40 and bulkhead 41 have opposed parts in the left and right shell parts 30 and 31, as seen in FIGS. 6 and 7.

Rear and front bosses 42 and 43 respectively extend rearward and forward from the cylindrical casing 44 of the motor 36, as seen in FIGS. 10 and 12), and are supported in corresponding coaxial recesses 45 and 46 in the rear end wall 40 and bulkhead 41 respectively, so as to support the motor casing 44 with respect to the shell 26. A flat 47 on the rear boss 42 (FIG. 9) co-acts with a corresponding flat in the surrounding recess 45 to prevent rotation of the motor casing 44 with respect to the shell parts 30 and 31, such that the motor 36 is antirotationally fixed within the shell 26.

The drive unit 25 further includes a transmission 50 (FIG. 5) coaxial with and forward of the motor 36. The transmission includes a reciprocating link member 51 and is driven from the forward extending, rotating output shaft 52 of the motor 36. The shaft 52 extends coaxially forward through the front boss 43 (FIG. 12) of the motor 36.

The transmission 50 (FIGS. 5 and 12) includes a pinion gear 53 fixed on the motor shaft 52 for rotation thereby, and a face gear 54 which, as seen in FIG. 12, underlies the pinion gear 53. The face gear 54 has a relatively large diameter central disk 56 carrying upward facing teeth 55 engaging corresponding teeth on the pinion gear 53 for rotation thereby. The face gear 54 includes a secondary pinion gear 57 fixed coaxially beneath the disk 56, and of substantially lesser diameter, which in turn drives a relatively large diameter output gear 60.

It will be understood that the pinion gear 53, face gear 54, secondary pinion 57 and output gear 60 are all provided with a full circumferential (360°) set of teeth, so that continuous rotation of the motor shaft 52 results in continuous rotation of the output gear 60. For convenience in drawing, some or all the gear teeth are not shown in various of the drawings, the toothed meshing connection of the gears therein thus being only schematically shown. See for example FIGS. 4, 10, 12, 13 and 14.

An output shaft 61 is fixed to and coaxially upstanding from the output gear 60 (FIG. 12) and fixedly rotatably drives an eccentric member 62 (FIGS. 5, 10 and 12) spaced above the output gear 60. In this embodiment, the output shaft is of rectangular cross-section to maximize its torque transmitting capability.

The eccentric member 62 comprises a radially extending disk 63 (FIG. 5) coaxial with the output shaft 61 and fixedly surmounted by an eccentric circular cylinder 64 eccentrically rotatable with the output shaft 61.

The link member 51 is generally T-shaped, as seen in FIG. 13, having a plate-like body 70 overlying the disk 63 of the eccentric member 62 and lying at right angles to the output shaft 61, and further having a plate-like fork 71 fixed at the rightward (FIGS. 5, 10, 12 and 13) end of the plate-like body 70 and extending in a plane substantially parallel to the output shaft 61. The plane of the plate-like fork 71 is perpendicular to the intended direction of reciprocating movement of the link member 51. The body 70, at its end portion remote from the fork 71, has an oblong through opening 72 snugly radially receiving the rotating eccentric cylinder 64 of the eccentric member 62, as seen in FIG. 10. More particularly, the length direction of the oblong opening 72 extends parallel to the plane of the fork 71 and is of sufficient length to accommodate 360° rotation of the eccentric cylinder 64 without movement of the body 70 parallel to the plane of the fork 71. On the other hand, the width of the oblong opening 72, namely in a direction perpendicular to the plane of the fork 71, corresponds substantially to the diameter of the eccentric cylinder 64, providing a sliding clearance between the body 70 and eccentric cylinder 64, so that rotation of the eccentric cylinder 64 will result in reciprocation of the link member 51 in a direction perpendicular to the plane of the fork 71.

The plate-like body 70 includes a thickened rim 73 (FIG. 5) around the oblong opening 72 and may thus be said to form a yoke for coaction with the eccentric cylinder 64. The side edges of the body 70 are preferably also thickened to form parallel longitudinal guide rails 74 (FIG. 10).

The above discussed moving elements of the transmission 50 are located and movably supported within the shell 26 as follows. The face gear 54 has coaxial downward and upward (FIGS. 5–7, 10 and 12) extending stub shafts 75 and 76 respectively rotatably supported in coaxial bearing bosses 80 and 81 respectively fixed on the opposing faces of the shell parts 31 and 30 (FIGS. 6, 7 and 12). Similarly, the output gear 60 and the eccentric member 62 have respective downward and upward extending stub shafts 82 and 83 coaxial with the output shaft 61 and rotatably supported in respective cylindrical bearing bosses 84 and 85 in the respective shells 31 and 30 (FIGS. 5–7 and 12). The link member 51 is slidably guided for reciprocation in a notch 90 (FIGS. 5 and 7) in the peripheral wall 91 of the left (upper in FIG. 5) shell part 30. The notch 90 has parallel opposed guide faces 92 (FIG. 7) spaced apart to snugly slidably guide therebetween the opposite guide rails 74 of the link member 51, and thus spaced at substantially at the maximum width of the link member. The thickness of the link member is guided for reciprocation between the peripheral edge 93 of the right (lower in FIG. 5) shell 31 and the width wall 94 (FIGS. 5 and 7) of the other shell part 30.

The central length axis LA (FIG. 10) of the link member intersects the central length axis MA of the motor shaft 52 at the axis SA of the output shaft 61 and stub shaft 83 (FIGS. 10 and 12), at an angle equal to the angle between the central length axis of the handle 12 and barrel 13 of the housing 11. Moreover, the length axes of the handle and barrel also intersect at the axis SA of the output shaft 61 when the drive unit 25 is installed in the handpiece housing 11 as hereafter discussed. In effect then, the link member longitudinal axis LA and motor shaft axis MA define the length axis of the barrel 13 and handle 12, respectively, when the drive unit 25 is installed in the handpiece housing 11.

Figure 3:
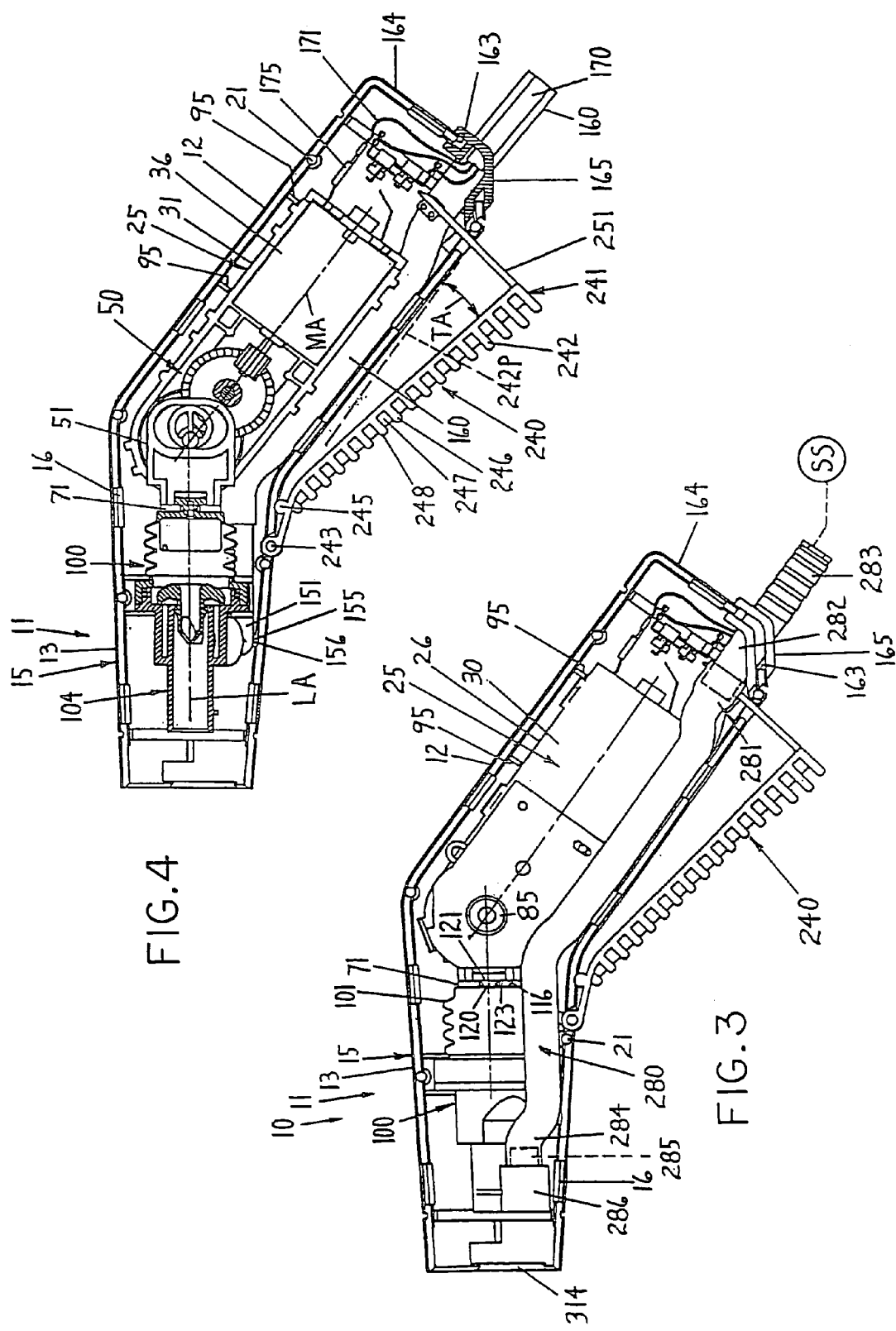
FIG. 3 is an enlarged elevational view of the FIG. 1 handpiece with the leftward housing part removed.

The drive unit 25 is located within the handle 12, as follows. As seen in FIGS. 3 and 4, transverse ribs 95 are molded into the interior surface of the handle 12 at opposing locations in the left and right housing parts 14 and 15 (FIGS. 2–4). For drawing convenience, only the ribs in the right housing part 15 are shown, the ribs in the left housing part 14 being compatible. The ribs 95 locate the drive unit 25 in the rightward/leftward direction in FIG. 2. Further, the drive unit shell bosses 84 and 85 (FIG. 5) protrude sideways from the drive unit shell and are pivotally received in corresponding hollow cylindrical bosses, one of which is shown at 96 in FIG. 2, and which extend toward each other from the interior of the left and right housing parts 14 and 15. The hollow cylindrical boss 96 of the left housing part 14 is not shown but is opposed to and compatible with the housing part 96 shown in the right housing part 15 of FIG. 2. The drive unit 25 is thus, except for the lateral positioning defined by the ribs 95, pivotally located within the handpiece housing 11 and is thus capable of some pivotal floating in the housing to achieve proper alignment of the longitudinal movement axis LA (FIG. 7) of the link member 51 with respect to the barrel 13 and a pump unit 100 (FIGS. 2–4 and 16–18) located in the barrel 13 as hereafter discussed.

Pump Unit

Turning now to the pump unit 100, attention is directed to FIGS. 2–4 and a6 18. The pump units includes a bellows 101 including an axially expandable and contractable, reciprocating, bellows wall 114 (FIG. 18) and a forwardly extending, rigid annular flange wall 102. Such flange wall 102 is loosely telescoped over a rigid, rearwardly extending annular flange 103 of a rigid, forwardly extending coaxial bellows housing 104.

The bellows 101 and bellows housing 104 are preferably of molded plastics material. A resilient O-ring 105 (FIGS. 16 and 19) is snugly radially disposed between the radially opposed, axially extending annular flanges 102 and 103, to create a fluid seal therebetween and hence between the bellows 101 and bellows housing 104, to prevent fluid leakage therebetween. The bellows 101 and bellows housing 104 have respective axially spaced radially extending steps 106 and 107 joined to the respective annular flanges 102 and 103 and axially spaced apart at a distance substantially greater than the diameter of the O-ring 105, as seen in FIG. 19. The axial extending flanges 102 and 103 and radially extending steps 105 and 106 define an annular chamber 110 in which the O-ring 105 is axially loosely, and radially snugly and sealingly, disposed. Note that the radially opposed surfaces of the axially extending annular flanges 102 and 103 are cylindrical, such that neither has an annular groove in which the O-ring seats. Thus, the O-ring is free to roll on the radially opposed cylindrical surfaces of the axially extending flanges 102 and 103 and the O-ring 105 does not significantly interfere with axial separation of the bellows 101 and bellows housing 104 from each other.

Instead, such axial separation is prevented, as hereinafter further discussed, by a forwardly-rearwardly (leftwardly-rightwardly in FIG. 2) spaced pair of ribs 111 (FIG. 2) extending radially inward from the interior wall of the right housing part 15 and a corresponding, laterally opposed pair of mirror imaged ribs (not shown) extending laterally inward from the interior wall of the left housing part 14. Such ribs 111 are also schematically indicated in FIG. 18.

The rear (right in FIG. 19) end of the bellows housing axial flange 103 abuts the radially extending step 106 of the bellows 101 and the forward (leftward in FIG. 19) end of the bellows axial flange 102 axially abuts a radial flange 112 which extends radially outward from and forwardly from the bellows housing step 107. The forward end of the bellows axial flange 102 thus radially overlaps the bellows housing step 107 in snug but axially slidable relation thereto. A small forwardly extending annular rib 113 protrudes forwardly from the bellows radial step 106 toward the O-ring 105 to prevent rearward escape of the O-ring 105 from the space between the axially extending flanges 102 and 103, in the event of slight axial shifting of the bellows 101 and bellows housing 104 away from each other.

The above mentioned radially inward extending ribs 111 of the handpiece housing 11 snugly axially oppose and sandwich therebetween the bellows radial step 106 and bellows housing radial flange 112 to positively prevent axial separation of the bellows 101 from the bellows housing 104, when the pump unit 100 is installed in the housing 11.

The above-mentioned bellows wall 114 extends rearward from the inner periphery of the radially extending annular step 106 of the bellows 101 (FIG. 18) and consists of an axially collapsible and extensible, flexible, wave cross-section, peripheral wall 114. The bellows wall 114 surrounds an axially expansible and contractible pumping chamber 115. At the rear end of the bellows 101, a radially extending drive end wall 116 closes the rear end of the bellows wall 114 and pumping chamber 115. A stub 120, having a radially enlarged head 121, is fixed to and extends coaxially rearwardly from the drive end wall 116.

To axially reciprocatingly drive (repetitively axially contract and expand) the bellows 101, the above discussed link member 51 (FIG. 5) of the drive unit 25 has its fork 71 provided with a central, radially opening, generally U-shaped slot 122 (FIGS. 11–13). The slot 122 divides the fork 71 into a pair of tines 123 (FIG. 11). The slot 122 opens leftwardly in FIG. 2, namely away from the rightward housing part 15 and toward the leftward housing part 14. Thus, with the drive unit 25 located in the right housing part 12 as seen in FIG. 3, the pump unit 100 can be inserted into the rightward housing part 15, with the stub 120 (FIG. 18) inserted in the slot 122 of the fork 71 (FIG. 11) so as to trap the tines 123 axially between the drive end wall 116 and head 121 of the bellows 101, as generally indicated in FIGS. 3 and 4. To prevent the bellows stub 120 from accidentally radially escaping out the open end of the slot 122 in the fork 71, the central portion 124 (FIG. 11) of the slot 122 is undercut by inward tapering of an intermediate portion 125 of the slot 122 as seen in FIG. 11. The tapered portion 125 of the slot 122 (FIG. 11) defines a snap fit detente for resiliently trapping the bellows stub 120 in the drive unit slot 122. Thus, to install the bellows stub 120 in the slot 122, the bellows stub 120 must be resiliently forced through the tapered portion 125 of the slot 122 and upon passing the latter, the stub resiliently snaps into the central portion 124 of the slot. The inner ends of the tapered portion 125 of the slot resiliently maintain the stub radially inboard thereof, in the central portion 124 of the slot 122.

The stub 120 and hence the bellows 101, and indeed the entire pump unit 100, is thus freely rotatable about its length axis with respect to the fork 71, so that the circumferential orientation of the drive unit 25 and the pump unit 100 is determined by the location thereof in the housing. The drive unit 25 and pump unit 100 are thus, to an extent, free to circumferentially float with respect to each other, about the connection of the stub 120 and fork 71, without interfering with the circumferential location of the drive unit 25 and pump unit 100 in the housing 11. Further, the edges of the slot 122, in particular of the central portion 124 thereof, are rounded in cross-section, as is the stub 120, to permit a modest amount of angular adjustment between the length axes MA and LA of the drive unit 25 and pump unit 100 and to allow the drive unit 25 and pump unit 100 to easily settle into their proper operating positions in the housing 11.

A cylindrical plug 126 is coaxially fixed to the interior side (left side in FIG. 18) of the bellows drive end wall 116 by a coaxial, rearward extending, undercut pin 127 snap fitted in a forwardly (leftwardly in FIG. 18) opening recess in the stub 120. The plug 126 has a diametral slot 130 opening forward from its front end and which faces forward toward a resilient valve member 131 (FIGS. 16 and 18) to maintain liquid communication between the central and radially outer portions of the pumping chamber 115.

The bellows 101 is thus a single element which carries out four different functions, namely sealing at the forward end, changing the pump chamber size in the middle thereof, the rearend acts as a piston and as a drive point. In addition, the front annular flange 102 helps locate the pump unit with respect to the housing barrel.

The pump unit 100 further includes a valve member 131, which is a one piece member of suitable resilient material and which by itself constitutes the entire moveable inlet and outlet valve system for the pump unit 100. More particularly, the valve member 131 comprises a short tubular central portion 132 (FIG. 18) which coaxially connects a forward (leftward in FIG. 18) tapering, duck bill type, outlet valve 133 and a rearwardly and radially outwardly extending umbrella type, inlet valve 134. The umbrella valve 134 is annular and has a central opening 135 which communicates coaxially from the pumping chamber 115 in the bellows 101 forwardly through the tubular central portion 132 and outlet duck bill valve 133 of the valve member 131.

Figure 18C:
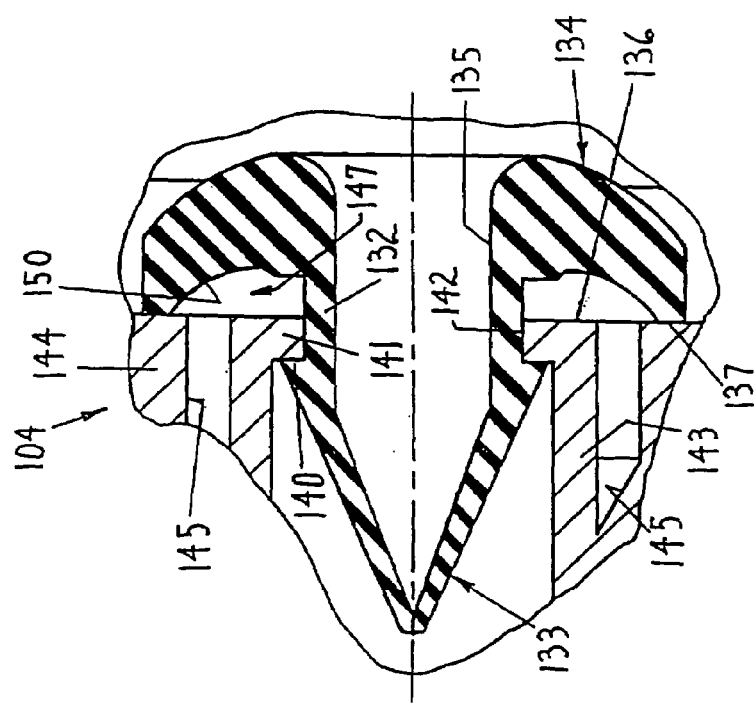
FIG. 18C is a fragmentary enlargement of FIG. 18 showing the valve member.
Figure 20:
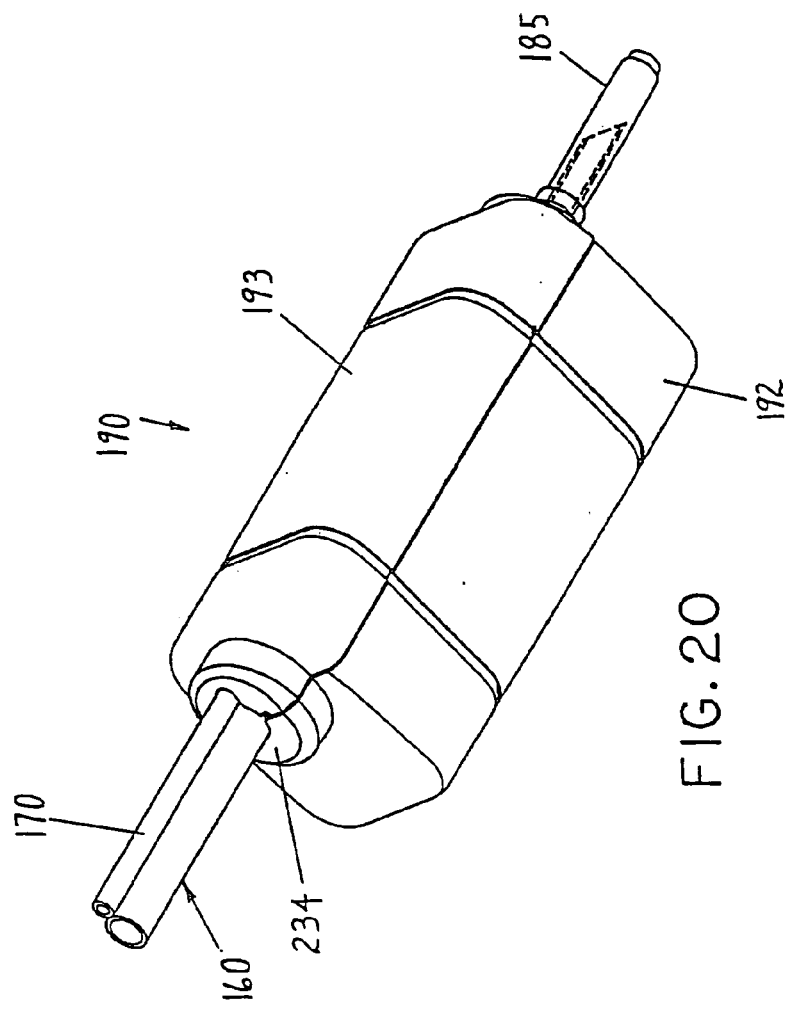
FIG. 20 is a pictorial view of the electric power supply unit connected to the FIG. 2 handpiece.
Figure 21:
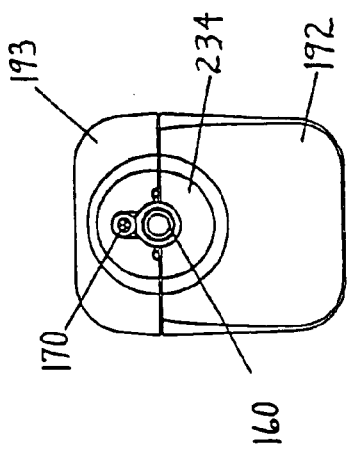
FIG. 21 is a left end view of the FIG. 20 electric power supply unit.

The bellows housing 104 comprises a rear (right in FIGS. 18 and 18C) facing recess having a perimeter defined by the annular flange 103 of the bellows housing 104 and a rear facing radial wall 136 which defines the front end of the pumping chamber 115. The umbrella valve 134 lies coaxially in the resulting recess 103, 136. The forward facing perimeter 137 of the umbrella valve 134, in its closed condition shown in FIGS. 18 and 18C, presses forward against the radial wall 136 to seal thereagainst. The valve member 131 is held against the right (rearward) movement away from the bellows housing wall 136 by axial interference between a rightward facing, radially outward extending, annular step 140 (FIG. 18C) at the rear (right) end of the duck bill valve 133, and a radially inward extending, leftward facing, annular flange 141 of the bellows housing 104. The radially inward directed, annular flange 141 is axially interposed between, and forms a port 142 between, the rear facing recess 103, 136 and a coaxial, forwardly extending, cylindrical, irrigation liquid outlet, discharge, conduit 143 (FIGS. 18 and 18C). The tubular central portion 132 of the valve member 131 extends snugly axially through the port 142.

To install the valve member 131 in the bellows housing 104, the tapered outlet duck bill valve 133 is pushed forward through the port 142, the bellows valve step 140 snaps forwardly (leftwardly in FIG. 18C) past the bellows housing flange 141, and the sealing perimeter 137 of the umbrella valve 134 is thereby pulled forwardly resiliently against the rearward facing bellows housing wall 136, leaving the valve member 131 with its duck bill valve 133 and umbrella valve 134 both in their closed condition shown in FIGS. 18 and 18C.

The bellows housing 104 further includes an annular liquid jacket 144 (FIGS. 18 and 18C) surrounding the rear portion of the liquid outlet conduit 143 and defining radially therebetween an annular liquid inlet chamber 145 (FIGS. 18, 18C and 19). The inlet chamber 145 communicates between a radial inlet port 146 (FIGS. 16 and 19), which opens radially outward through the side of the bellows housing 104, and an annular space 147 (FIG. 18C). The annular space 147 is bounded by the forward face 150 and tubular central portion 132 and sealing perimeter 137 of the umbrella valve 134 and the radial face 136 of the recess 103, 136 of the bellows housing 104.

Thus, a rightward pullback of the bellows head 121 axially expands the bellows, from its FIG. 18A position towards its FIG. 18 position. This reduces the pressure within the bellows. This in turn keeps the duck bill valve 133 closed and pulls the sealing perimeter 137 of the umbrella valve 134 rightwardly away from the bellows housing recess radial wall 136 and draws liquid from the port 146 through the annular inlet chamber 145, around the perimeter 137 of the open umbrella valve and into the interior of bellows.

On the other hand, a leftward push forward of the bellows head 121 axially compresses the bellows from its FIG. 18 position toward its FIG. 18B position and raises the pressure in the bellows, to close the umbrella valve 134 and open the duck bill valve 133 and force a pulse of liquid out of the bellows forwardly through the duck bill valve 133 and liquid outlet conduit 143.

Figure 16:
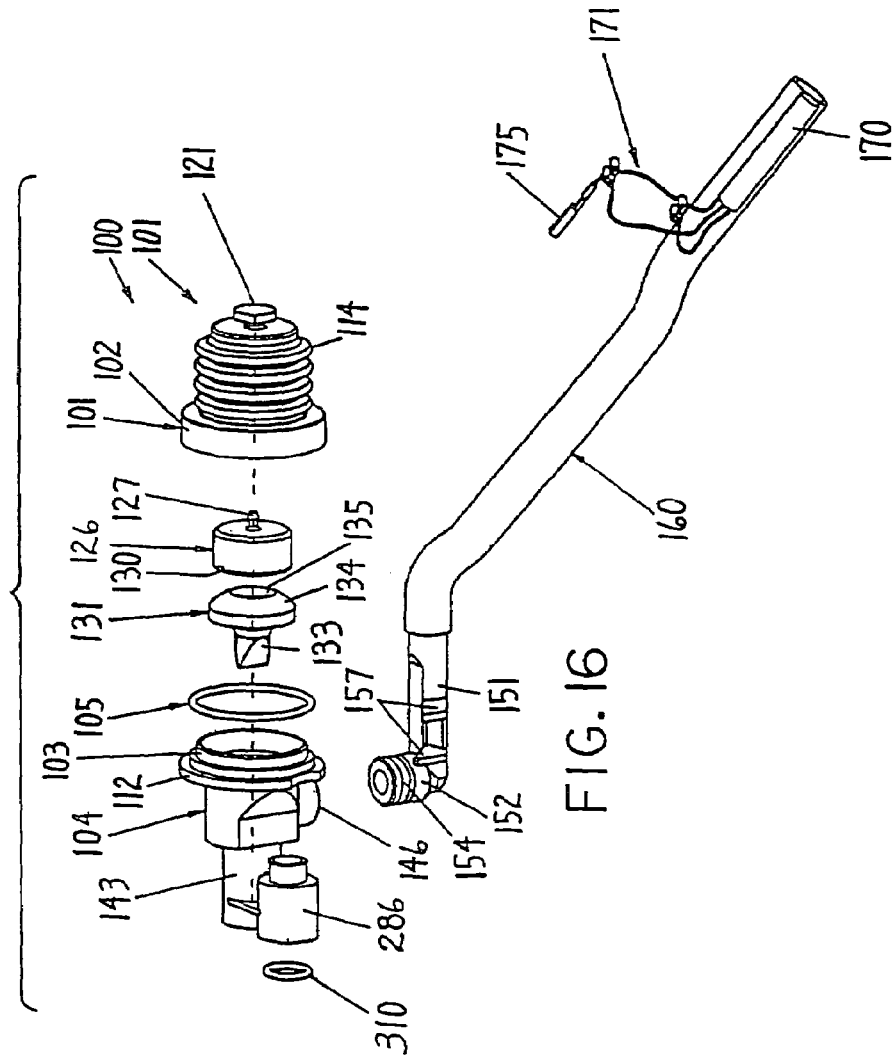
FIG. 16 is an exploded pictorial view of the pump unit of FIG. 2 in an enlarged scale.
Figure 17:
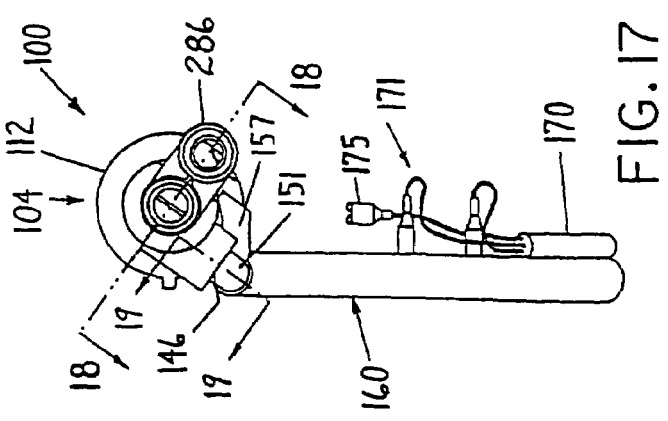
FIG. 17 is a front end elevational view of the pump unit of FIG. 16 taken substantially from the left side of FIGS. 2–4 and 16.

Irrigation liquid is drawn to the inlet port 146 of the bellows housing 104 through an elbow 151 (FIG. 19). The outlet end 152 of the elbow and the inlet port 146 are cylindrical, with the elbow outlet end 152 being a snug axially sliding fit in the inlet port 146. An axially elongate, annular groove 153 in the outer periphery of the elbow outlet 152 houses a seal ring, here an O-ring, 154 which bears sealing and rollingly on the radially opposed and surrounding surface of the inlet port 146 to prevent liquid leakage out of the elbow 151 at its interface with the inlet port 146. The elbow 151 is not mechanically interlocked with the inlet port 146 but can slide in and out with respect thereto. The elbow 151 is held in place with its outlet end 152 sealingly within the port 146 by bearing of a portion 155 (FIG. 4) of the handpiece housing barrel 13 against the outboard surface 156 of the elbow 151, with the pump unit installed in the handpiece housing 11. The elbow 151 here fixedly carries a pair of parallel fins 157 (FIGS. 16, 17 and 19). The fins 157 extend radially from the rear inlet end portion of the elbow 151 and axially sandwich therebetween the flanges 106 and 112 of the bellows 101 and bellows housing 104, at least to help the housing ribs 111 (FIG. 18) fins 157 prevent axial separation of the bellows and bellows housing. The housing ribs 111 and fins 157 are more or less evenly circumferentially located around the bellows 101 and bellows housing 104.

An elongate flexible irrigation liquid supply hose 160 (FIGS. 2, 4, 16, 17, 19, 22, 23, 25 and 29) has a forward end 161 which telescopes sealing and fixedly over the rear end 162 of the elbow 151 as seen in FIGS. 19 and 29. Although an annular barb is shown at 162 (for example in FIG. 19) a barbless, cylindrical end 162 is satisfactory. In the assembled handpiece, the irrigation liquid hose 160 extends rearward from the elbow 151 (FIG. 4) in the barrel 13 of the housing and angles downwardly and rearwardly along the bottom of the handpiece handle 12 to exit rearwardly and downwardly through a hole 163 (FIG. 2) in the bottom end wall 164 of the handpiece housing 11. A clamp plate 165 (FIGS. 2, 3 and 4) of bent cross-section has a perimeter groove 166 for receiving the edges of the hole 163 in the housing bottom end wall 164, such that the clamp plate 165 is trapped in and partly closes the hole 163 in the bottom end 164 of the housing handle 12 when the housing is fully assembled. A notch 167 (FIG. 2) in the rightward end of the clamp plate 165 permits exit therethrough of irrigation liquid supply hose 160 from the handpiece housing 11 and snugly and frictionally grips such hose, without crushing or collapsing it, so that such hose 160 cannot easily be pulled out of the housing 11 or off the elbow 151.

The irrigation liquid hose 160, the inlet line, integrally therewith, a smaller diameter rib 170 (FIGS. 2, 16, and 17) A plurality (here three) insulated electrical conductors (wires) 171 have intermediate portions contained within and extending the length of the rib 170. Forward end portions of the insulated wires 171 emerge from the forward end of the rib 170 and carry conventional electrically conductive connectors 175. The forward end of rib extend through the notch 167 (FIG. 2) and ends just inside the bottom portion of the handle of the housing 11, as seen in FIG. 4. The forward ends of the conductors, carrying the connectors 175, extend into the lower portion of the handpiece handle 12. Thus, as apparent from the below description, rib 170 functions as a cable through which conductors 171 extend from the battery pack to the handpiece housing 11.

The insulated electrical conductors 171 extend along the length of the central portion of the liquid supply hose 160 and have rear ends provided with respective electrically conductive connectors 176 (FIGS. 22 and 29), such that electric current can flow from a given rear connector 176 through its corresponding insulated electrical conductor 171 and to its corresponding front electrically conductive connector 175 in a conventional manner. Short rear portions of the conductors 171 are loose and moveable with respect to the liquid supply hose 160 as seen in FIGS. 22 and 29.

The electrical connectors 175 and 176 are conventional crimp type connectors.

Instead of being molded in or otherwise constrained within the generally circular cross section rib 170 in FIG. 2, the elongate central portion of the insulated electrical conductors 171 may be fixed side by side, in a flat array, to the outside of the liquid hose 160, as shown in FIGS. 22 and 29, and such can be accomplished by adhesive bonding or by any other convenient means.

The hose 160, 170 thus serves the dual use of conveying both irrigation liquid and electric operating power.

The length of the central portion of the liquid hose 160, to which the insulated conductors 170 are fixed, preferably extends several feet (for example 8 to 10 feet) from the handpiece 10. The rear end 177 (FIGS. 22 and 23) of the liquid hose is here provided with a fitting 180 of hollow tubular construction open to axial liquid flow therethrough. The fitting 180 comprises a forward end portion 181 (FIG. 23) fixed sealingly telescoped in the rear end 177 of the liquid hose 160, a square central flange 182 (FIG. 22) and a rear end portion (or "spike") 183 having a sharpened tip 184. The tip 184 is capable of conventional insertion into a conventional source S (FIG. 22) of irrigation liquid, for example a conventional supply bag, for conveying irrigation liquid therefrom forward into the hose 160. The square flange 182 prevents rotation of the fitting 180 in the casing 191, which helps when removing the spike 183 from the liquid supply bag. In the embodiment shown, the rear end portion 183 is covered by a protective cap 185 prior to use so that the sharpened tip 184 will not accidentally be dulled.

Thus, the length of the liquid supply hose 160 allows the irrigation liquid source S to be located at a distance from the handpiece and thus out of the way of the surgical personnel at the operating table where the handpiece 10 is to be used.

Electrical Power Supply Unit

To provide operating electrical power to the motor 36, a compact, self contained electrical supply unit 190, a battery pack, (FIGS. 20–25 is fixed on the rear portion of the liquid hose 16O. The power supply unit is thus located remotely from the handpiece 10, adjacent to the source S of irrigation liquid.

The power supply unit 190 comprises a casing 191 preferably of rigid molded plastics material. The casing 191 here comprises a relatively deep, substantially rectangular pan 192 (FIG. 2) whose top (as oriented in FIGS. 22 and 23) is fixedly closed by a cover 193. The pan 192 has front and rear end walls 194 and 195 (FIGS. 23, 23A and 24) having fixed upward opening slots 200 each defined by a laterally spaced, opposed pair of U-shaped flanges 201 (FIGS. 23A and 23B). The slots 200 are undercut in that each has a mouth 202 laterally narrower than the remainder of the slot 200 and communicating between the remainder of the slot 200 and the interior cavity of the pan 192. The undercut slots 200 are of constant cross-sectional size and shape vertically (i.e. into and out of the page in FIG. 24 and up and down in FIG. 23).

For convenient reference in the drawings, the reference numerals 200 and 201 are suffixed, so that the undercut slots and U-shaped flanges on the front pan wall 194 are indicated by the reference characters 200F and 201F and the undercut slots and U-shaped flanges on the rear pan wall 195 are indicated at 200R and 201R.

The U-shaped flanges 201F defining the slots 200F on the forward end wall 194 start substantially from the pan bottom wall 196 and extend a bit less than half way up the front end wall 194.

On the other hand, the U-shaped flanges 201R of the slots 200R on the rearward end wall 195 of the pan are spaced above the bottom wall 196 of the pan upon respective block-like pillars 203 which define an up-facing bottom 204 for each of the U-shaped flanges 201R on the rear pan wall 195.

Rising from bottom wall 196 of the pan between the two central pillars 203 to a height below the bottoms 204 of the slots 200R thereof, is a central block 205 from which forwardly extends, along the pan bottom wall 196, a T-shaped flange 206 (FIG. 23B) of constant cross section vertically and defining a pair of vertically open and laterally oppositely opening grooves 207 disposed immediately forward from the two central pillars 203 on the rear pan wall 195.

Two such undercut slots 200F are spaced symmetrically side by side on the front pan wall 194. Similarly, and at the same effective lateral spacing, two such slots 200R are spaced laterally side by side on the pan rear wall 195.

Springy, electrically conductive sheet metal battery contacts of three different kinds are indicated at 210 and 211 and 212 and FIGS. 26, 27 and 28 respectively.

A pair of such contacts 210 are provided and each comprises a generally rectangular foot 213 adapted to snugly slide down into a respective undercut slot 200F at the pan front wall 194. Each foot 213 is provided with resilient toes 214 angled out of the plane of the foot 213 and adapted to bite against the interior of the corresponding undercut slot 200F to fix the corresponding battery contact 210 in place therein.

Similarly, each of a pair of battery contacts 212 (FIG. 28) has a resilient fork-shaped foot 215 adapted to fit snugly and slidingly down into the corresponding undercut groove 200R at the rear wall 195 of the pan 192 and with springy toes 216 for fixedly gripping the interior of the corresponding undercut slot 200R.

In a generally similar manner the single, low speed battery contact 211 (FIG. 27) has a resilient U-shaped foot 217 for sliding down over the T-shaped flange 206 (FIG. 23B), with springy toes 218 bent out of the plane of the foot 217 for bitingly engaging the walls of the grooves 207 of the T-shaped flange 206.

Each of the battery contacts 210, 211 and 212 thus slides with its corresponding foot into the desired location with respect to the grooves 200F, 200R and 207 and locks fixedly therein. This is generally indicated in FIGS. 22–24. The battery contacts 210, 211 and 212 have respective resilient fingers 221, 222 and 223 (FIGS. 26, 27 and 28 respectively), two each for the battery contacts 210 and 211 and one each for the battery contacts 212. Such fingers 221, 222 and 223 protrude from the respective slots 200F, 200R and 207 into the interior of the pan 192 for electrically contacting batteries 230 (FIG. 22) to be housed in the pan 192. Further, the battery contact 211 and each of the battery contacts 212 (FIGS. 27 and 28 respectively) have an upstanding terminal (224 and 225 respectively) of simple rectangular shape for releasable telescoped engagement within a respective one of the connectors 176 at the rear ends of the three insulated electrical conductors 171 (FIG. 22).

Turning now to the arrangement of the batteries 230 within the pan 192, one embodiment according to the invention advantageously uses batteries of a kind widely available in retail stores, namely AA size alkaline batteries. In addition to their wide availability to the public, these batteries advantageously are inexpensive, have a long shelf life and provide full operating voltage until almost fully discharged. In the embodiment shown, eight such batteries 230 are provided and are individually indicated at B1, B2, B3, B4, B5, B6, B7 and B8. As shown in FIGS. 22–24, ribs 231 extending circumferentially within the pan 192 cradle the batteries 230 fixedly but removably within the pan 192. The polarity of the eight batteries is indicated by "plus" signs marked thereon. As seen in the drawings, the batteries 230 are arranged in four rows of two head-to-tail batteries each. Four of the batteries 230 lie in the bottom (FIGS. 22 and 23) of the pan in two rows of two each and the remaining four batteries 230 lie on top of those.

Figure 22A:
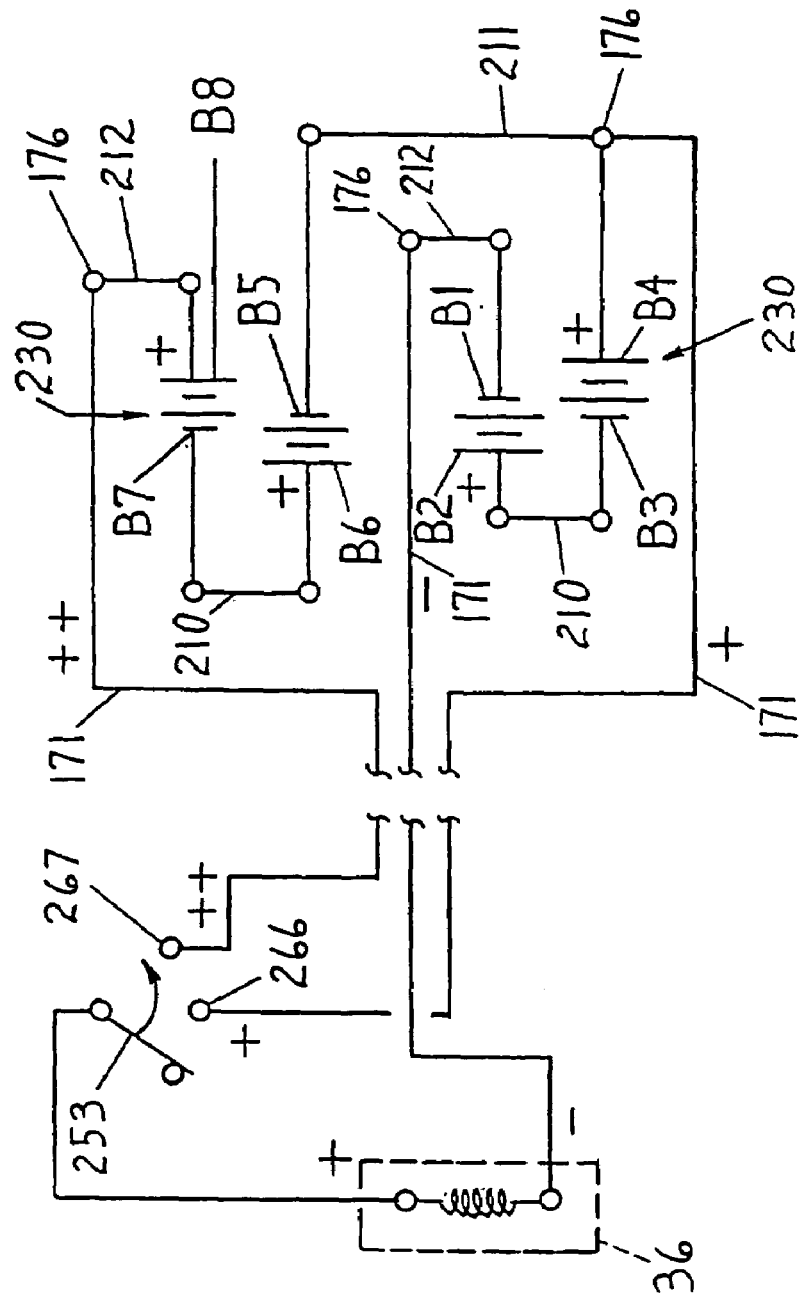
FIG. 22A is an electrical schematic of the FIG. 2 handpiece and FIG. 20 electric power supply unit.

The ends of the battery rows bear variously on the above discussed battery contacts 210, 211 and 212 as generally indicated for example in FIG. 22 and also in the schematic circuit drawing in FIG. 22A. More particularly, the four batteries B1, B2, B3 and B4 defining a vertical plane nearest to the viewer in FIG. 23 are connected in series from the near connector 212 leftwardly through the top row of batteries, down through the near upstanding connector 210 and thence rightwardly through the bottom pair of batteries to the lower rear connector 211. The remaining four batteries B5–B8 are arranged in a vertical plane behind above-mentioned batteries B1–B4. More particularly, the batteries B5–B8 connect in series from the far side of the lower rear connector 211 forwardly (leftwardly in FIG. 22) to the far connector 210, upwardly therethrough, and then rearwardly back to the far upper connector 212.

The cover 193 (FIGS. 23 and 25) has plural, laterally extending, depending ribs 232 (FIGS. 23 and 25) intended to seat upon the uppermost batteries B1, B2, B7 and B8 and fix the batteries B1–B8 in the pan with the cover 193 fixed in its normal closed position atop the pan 192. The cover is fixedly securable atop the pan by any convenient means, such as snap fit connectors, a portion of which are generally shown in 233 in FIG. 22, and generally like those discussed above with respect to the handpiece housing 11, as at 16, and as generally discussed with respect to the drive unit shell 26, as at 32, 33.

The aforementioned rear end 177 of the hose 160 extends through the casing 191 along the horizontal parting plane between the pan 192 and cover 193, and so lies close adjacent the topmost batteries B1, B2, B7 and B8.

Hollow front and rear bosses 234 and 235 (FIGS. 23 and 25) extend forward and rearward respectively, from the casing 191. At the parting plane between the pan 192 and cover 193, the bosses 234 and 235 are notched (for example at 236 in FIG. 22) for extension therethrough of the rear end 177 of the liquid hose 160. The rear hollow boss 235 is sized and shaped to receive radially therein the square flange 182 (FIG. 23) on the rear end of the liquid hose 160, and thereby axially fix the rear end of the liquid supply hose 160 within the casing 191 and nonrotatably fix the fitting 180 to the battery casing 191. The notch 236 in the front boss portion 234 on the cover 193 is indented by one or more small recesses 237 for receiving axially therethrough the rib 170 containing the insulated electrical conductors 171, whose rear end connectors 176 are respectively fixed to the terminals 224 and 225 of the battery contacts 211 and 212.

Trigger Unit

The handpiece 10 further includes a trigger unit 240 (FIGS. 2–4) for controlling actuation of the motor 36 and, by extension, pump unit 100. The trigger unit 240 comprises a generally L-shaped trigger member 241 (FIGS. 2, 4 and 4A), that functions as a control switch, and that comprises an elongate trigger lever 242. The upper, forward (leftward in FIGS. 2 and 4) end of the trigger lever is pivoted by laterally extending integral pins 243 pivotally receivable in suitable holes in laterally opposed bosses (one of which is shown in FIG. 2) in the opposed lower edges of the housing parts 14 and 15, near the rear end of the barrel 13. Snapping together of the two housing parts 14 and 15 thus captures the pivot pins 243 and pivotally mounts the trigger with respect to the handpiece housing.

The trigger lever 242 includes a transverse ridge 245 (FIG. 4) near to but spaced rearwardly from the pivot pins 243 and facing the underside of the barrel 13 and adapted to bear on the underside thereof in the manner of a fulcrum. By far the major length 246 of the trigger lever 242 is to the rear (right in FIG. 4) of the fulcrum ridge 245. This rearward trigger part 246 is relatively rigid in the portion thereof spaced at least somewhat to the rear of the fulcrum ridge 245. Such rigidity is assisted by a forward facing longitudinal reinforcement rib 247 extending rearward along the front face of the trigger lever 242 from a point near the fulcrum ridge 245. The front of the trigger lever 242, to the rear of the fulcrum ridge 245 is, in the embodiment shown, provided with transversely extending ribs 248 to provide the user with a non-slip grip of the trigger lever 242.

The trigger lever 242 is bendable near the fulcrum ridge 245, both to the front and rear thereof, in a resilient manner. In this way, the resilience of the trigger lever tends to hold it in its forward, inactive position shown in FIG. 4, with the fulcrum ridge 245 bearing on the underside of the handpiece barrel 13. On the other hand, when the user grips the handle 12 and squeezes the trigger lever 245 toward it, in the direction indicated by the arrow TA in FIG. 4, the trigger lever bends in the region of the fulcrum ridge 245, tending to straighten from its relaxed convexly forwardly curved configuration of FIG. 4, so that the rear face of the trigger lever can be pulled into the dotted line position 242P, substantially against the front face of the handle 12. Upon release of the trigger by the user, the natural resilience of the trigger lever 242 unbends it back to its solid line forward position shown in FIG. 4. Accordingly, the trigger naturally returns forward to its non-operative position without need for a separate return spring.

The trigger arm 251 fixedly carries a thumb 250 (FIG. 4A) intermediate it ends in the housing handle 15 and which interferes with the housing wall adjacent the hole 252, to prevent the resilient restoring force of the trigger lever 242 from pulling the trigger arm 251 leftwardly (FIG. 4A) out of the housing handle 12.

A plank-like switch contact support arm 251 (FIGS. 2, 4 and 4A) protrudes substantially at a right angle from the rear, or bottom, end of the trigger lever 242 and extends upwardly and rearwardly (in FIG. 4) into the lower portion of the handle 12, loosely through a hole 252 (FIG. 4A) in the opposing bottom wall of the handle. A plate-like electrically conductive contact blade 253 fixedly extends through the thickness of the arm 251, and has a front portion exposed towards said motor and a rear portion exposed toward the bottom end 164 of the handpiece handle.

A pair of rectangular posts 255 and 256 protrude fixedly into the interior of the handle 12 from the inside of the right housing part 15, about midway between the drive unit 25 and the housing bottom end 164 (FIGS. 4A and 4B). Each post 255 and 256 includes a T-shaped flange 260 extending substantially forward toward the drive unit 25. Each T-shaped flange 260 defines a pair of oppositely facing grooves 261 (FIG. 4C).

Electrically conductive, spring-like metal contacts 262 and 263 (FIGS. 4A and 4C) each have a substantially U-shaped foot 264 for reception on the T-shaped flange 260 of the corresponding posts 255 and 256. The contacts 262 and 263 further each have a substantially rectangular, projecting terminal 265 for telescopic fixing thereon, in electrically connected relation, a corresponding one of the front connectors 175 of the three insulated electrical conductors 171. The electrical contacts 262 and 263 further have respective, generally L-shaped, plate-like, flexible contact leaves 266 and 267 (FIG. 4C). The contact leaves 266 and 267 extend toward the drive unit 25 as seen in FIG. 4A.

Protruding rearwardly from the motor 36 are a pair of electrically conductive contacts 270 and 271 (FIGS. 4A and 9). The contact 271 is a conventional terminal (like those at 224, 225 and 265) for receiving one of the front connectors 175 in fixed and electrically conductive relation thereon.

In contrast, the contact 270 is an elongate, springy rectangular piece, bent intermediate its ends in dogleg fashion, and angling from the rear end of the motor 36 rearwardly and somewhat rightwardly (in FIG. 4A) to a free end portion spaced near the contact leaves 266 and 267.

Gradual pressing of the trigger lever 242 toward the handle housing (rightwardly in FIGS. 4 and 4A) moves the arm 251 and hence the contact blade 253 progressively further into the handle 12 through a series of positions, three of which are indicated in broken lines at 253A, 253B and 253C in FIG. 4A.

The free (rightward in FIG. 4A) end of the arm 251 is beveled at 272 to help it ride over the contacts 266 and 267 as the trigger lever 242 is sequentially squeezed more and more toward the handle 12. The arm 251 is progressively resiliently bent, like a leaf-spring, as its free end rides over the fixed contacts 266 and 267, to firmly press its contact blade 253 against the latter.

Thus, as the trigger lever 242 is pressed toward the handle 12, the beveled free end of the arm 251 rides over the contact leaf 266 past its dotted line position 253A and toward its dotted line position 253B. As the free arm end approaches position 253B, the contact blade 253 slides into electrical contact with the contact leaf 266 and the motor contact 270 to establish electrical connection therebetween. The motor contact 270 resiliently bends to allow continued travel of the contact blade 253 and arm 251 further into the handle, as indicated in dotted line at 270B, and to press firmly against the contact blade 253. Given only a light pull on the trigger lever 242, the arm 251 and contact blade 253 tend to stop in the position indicated in dotted lines at 253B, by reason of the free end of the arm 251 colliding with the contact leaf 267. In this "B" position, electric current is fed to the motor 36 only from half the battery collection, namely batteries B1, B2, B3 and B4 in FIG. 22A. The motor 36 thus runs at only a preselected fraction of its full speed and the pump unit 100 outputs irrigation liquid pulses at a desired frequency and amplitude, which are less than the maximum available. The apparatus is thus operated in its low output mode. The colliding of the free end of the trigger arm 251 with the contact leaf 267 gives tactile feedback to the user, that the low output mode of the handpiece has been selected.

Further pulling in of the trigger lever 242 by the user causes the beveled free end of the arm 251 to bend rightwardly (FIG. 4A) the contact leaf 267 to a dotted line position indicated at 267C, allowing the free end of the arm 251 to override the contact leaf 267, such that the contact blade 253 moves into its "full-pull" dotted line position 253C and further bends the motor contact 270 its dotted line position 270C. In this final position, the contact blade 253 establishes electrical contact between the motor contact 270 and the contact leaf 267, thereby applying the full series voltage of all eight of the batteries B1–B8 to the motor 36 to operate the latter at its full speed and thereby drive the pump unit 100 at its full output, namely to provide irrigation liquid pulses out of the pump unit 100 at maximum pulse amplitude and frequency.

When the user releases the trigger lever 242, the resiliently bent trigger lever 242, due to its inherent resilience, springs back from its fully pulled-in position indicated in broken lines at 242P, to its solid line rest position indicated at 242 (FIG. 4A). The electrical connection between the contact 262 or 263 and the contact 270 is broken.

Suction Hose

A flexible suction hose 280 (FIGS. 2 and 3) is led along within the housing (within the lower part of the housing in FIG. 3) past the drive unit 25 and pump unit 100. The above-mentioned clamp plate 165 includes a tubular structure molded thereinto and defined by a forward nipple 282 in the handle 12 and, in coaxial fluid communicating relation therewith, a rearward nipple 283 which extends rearwardly out of the bottom end 164 of the handpiece handle 12. The rear end portion 281 of the suction hose 280 is sealingly and fixedly telescoped over the front nipple 282. A conventional flexible hose, not shown, is conventionally and sealing telescopable over the rear nipple 283 for connecting same to a conventional suction source, as schematically indicated at SS in FIG. 3.

The front end portion 284 of the suction nose 280 is sealingly telescoped over a rearward opening nipple 285 on a short suction conduit 286 (FIGS. 2, 3, 16, 17 and 18). The suction conduit 286 (FIG. 18) is fixed side by side, in piggyback fashion, on the periphery of the irrigation liquid conduit 143 and hence is a part of (preferably an integral plastic molded part of) the bellows housing 104.

The clamp plate 165 serves several purposes. It provides a suction hose connection, bears on the irrigation liquid hose where it enters the handpiece housing, and helps align the rear (rightward in FIG. 4) end wall portions of the housing halves as they are assembled together, and in so doing, is itself fixed on the housing. In addition, the clamp plate 165 is of one piece, preferably a plastic molding, and is partially recessed into the handpiece so that it does not make the handpiece look any bigger.

Tip Unit

Figure 8:
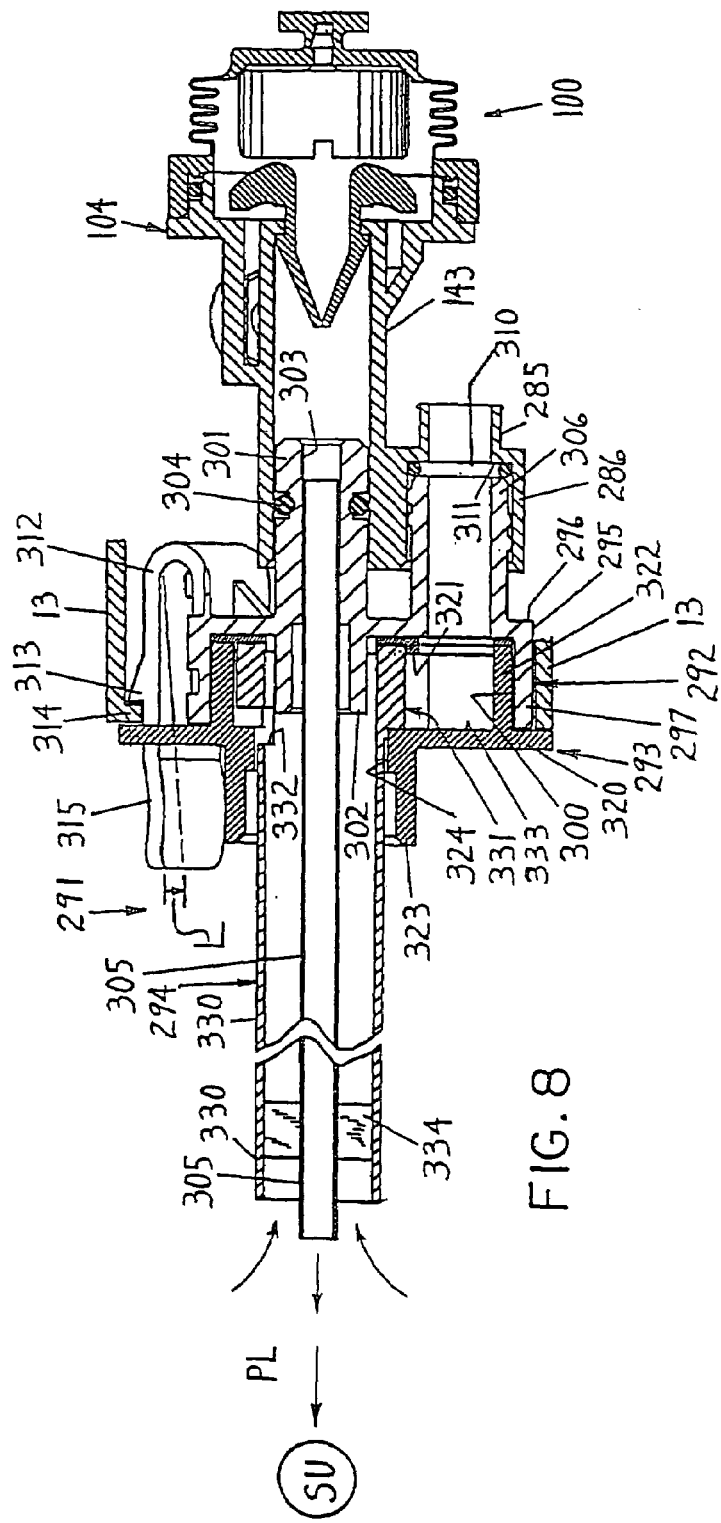
FIG. 8 is an enlarged central cross-sectional view of a tip unit usable with the handpiece of FIG. 2 and showing same installed in a pump unit shown in central cross-section substantially as in FIG. 4.
Figure 8A:
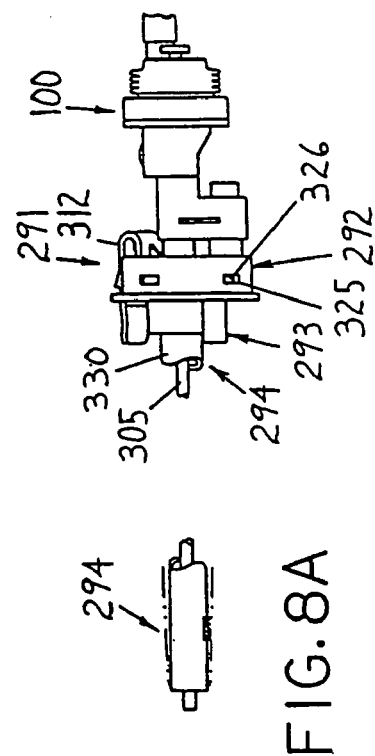
FIG. 8A is a reduced size, fragmentary, side elevational view of the apparatus of FIG. 8.
Figure 8B:
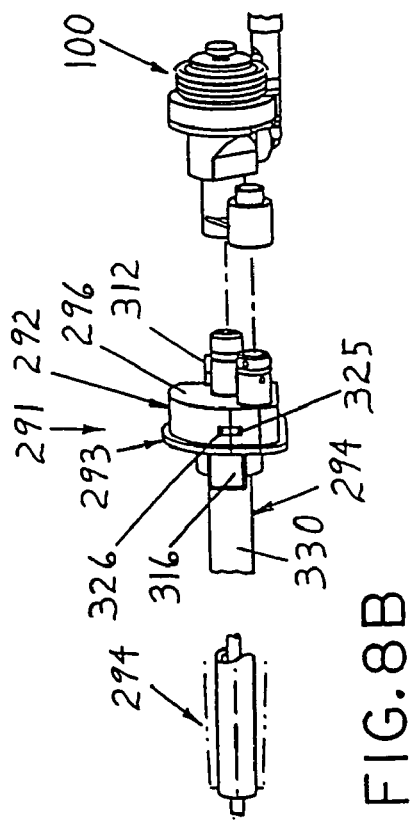
FIG. 8B is a pictorial view of the apparatus of FIG. 8A.

A tip unit 291 (FIGS. 8, 8A and 8B) is releasably fixable on the front end of the handpiece 10 and extends forward therefrom for applying irrigation liquid pulses and/or suction to a surgical site indicated schematically at SU in FIGS. 8 and 8B. The tip unit 291 (FIG. 8) comprises a coupling 292, a front cover 293 fixed to the front of the coupling 292, and an elongate hollow wand 294 extending forwardly from the coupling and front cover for aiming at a surgical site SU. The coupling 292, cover 293 and wand 294 are preferably one piece molded plastic units. The wand 294 is preferably of clear plastics material.

The tip unit 291, and more specifically the coupling 292, is releasably fitted in fluid tight relation to the front of the bellows housing 104 of the pump unit 100 and is releasably latched within the open front end of the handpiece housing barrel 13 as hereinafter discussed.

More particularly, the coupling 292 (FIG. 8) comprises a shallow, forward opening cup 295 having a flat base wall 296 from which forwardly extends a shallow peripheral wall 297, thereby defining a forward opening recess 300. Coaxial irrigation liquid nipples 301 and 302 extend fixing rearwardly and forwardly, respectively, from the base wall 296 and together define a coaxial bore 303 therethrough and through the base wall 296. The rear nipple 301 is snugly but slidably receivable rearwardly into the open front portion of the liquid outlet conduit 143 of the bellows housing 104. An O-ring 304 seats in an annular groove outward facing on the rear nipple 301 and sealingly engages the interior of the liquid outlet conduit 143 to prevent irrigation liquid leakage therebetween.

The wand 294 includes a coaxial, relatively small diameter, irrigation liquid outlet tube 305 which at its rear end is telescoped fixedly and sealingly within the bore 303 of the front and rear nipples 301 and 302 for receiving a pulsed flow of irrigation liquid from the irrigation liquid outlet conduit 143 of the bellows housing 104.

The coupling 292 further includes a suction nipple 306 fixedly extending rearward from the base wall 296 in spaced parallel relation with the irrigation liquid nipple 301. The suction nipple 306 is snugly insertable rearwardly coaxially into the front opening suction conduit 286 of the bellows housing 104. An O-ring 310 is axially sandwiched between the rear end of the suction nipple 306 and a front facing annular step 311 at the rear end of the suction conduit 286 to prevent leakage therebetween.

The coupling 292 further includes a leaf spring-like, generally U-shaped latch arm 312 which extends rearward from the peripheral portion of the base wall 296, curves radially outwardly and forwardly, and extends forward past the front cover 293, in radially outwardly spaced relation from the wand 294. A wedge-shaped, transverse ridge 313 on the exterior base of the latch arm 312 is approximately centered between the front and rear ends of the latch arm. A circumferentially extending, radially inward protruding rib 314 (FIGS. 2, 3 and 8) on the interior face and at the open front end of the right housing part 15 (at the front end of the barrel 13) opposes the latch arm 312, immediately ahead of the ridge 313, with the tip unit 291 installed on the front end of the handpiece 10 as shown in FIG. 8. The ridge 313 has a front facing step which abuts interferingly with the housing rib 314 to releasably block removal of the tip unit from its installed condition shown in FIG. 8. To remove the tip unit from the front end of the handpiece, the user simply presses radially inward against the forward protruding end portion 315 of the springy latch arm 312, sufficient to radially inward displace the ridge 313 out of interfering relation with the rib 314 and thereby unlatch the tip unit from the front end of the handpiece. This allows forward removing the tip unit 291 from the open front end of the handpiece barrel 13 and removing of the irrigation liquid and suction nipples 301 and 306 from the liquid outlet conduit 143 and suction conduit 286 of the bellows housing 104.

The tip unit 291, or any alternative tip unit having a substantially identical coupling and front cover, can be installed operatively on the front end of the handpiece 10 by inserting same into the open front end of the handpiece barrel 13 so that the nipples 301 and 306 enter the liquid and suction conduits 143 and 286 respectively, to their position shown in FIG. 8. During this installation, the forward facing slope of the wedge cross-section transverse ridge 313 slides rearwardly past the housing rib 314, bending the springy latch arm 312 radially inward as generally indicated by the arrow L in FIG. 8, so that the wedge cross-section ridge 313 can snap rearwardly past the rib 314 at the open front end of the housing barrel 13. Thus, the tip unit 314 can be slid axially into the front end of the barrel 13 and upon reaching its innermost position latches itself against unintended removal. In its installed condition of FIG. 8, the tip unit is substantially rigidly fixed with respect to the front end of the bellows housing 104 and hence with respect to the handpiece barrel 13.

The front cover 293 (FIG. 8) comprises a plate 320 which extends radially of the wand 294 and of the length axes of the barrel 13 and the pump unit 100. The peripheral shape of the plate 320 conforms to the cross-sectional shape of the front end of the barrel 13, so that the perimeter of the plate 320 is substantially flush with the outer periphery of the open front end of the barrel 13, and so that the plate 320 effectively covers the open front end of the barrel 13. The peripheral shape of the plate 320 and cross-sectional shape of the front end of the barrel 13 in one embodiment is generally D-shaped, with a generally flat underside and a convexly curved top and sides. The plate 320 is not intended to seal the open front end of the barrel 13 and so need not tightly abut same. Since the peripheral wall 297 of the cup 295 fits easily within the open front end of the barrel 13, the plate 320 extends radially outwardly beyond the cup 295, as seen in FIGS. 8, 8A and 8B.

The front cover 293 includes an annular flange 322 extending axially rearwardly therefrom, radially snugly into the cup 295 of the coupling 292 to bottom rearwardly and sealingly against a resilient gasket 321 which is disposed against the front face of the base wall 296 of the cup 295. Respective holes in the gasket 321 loosely surround the front nipple 302 and leave fully open the communication between the interior of the suction nipple 306 and the interior of the cup 295. The front cover 293 further includes a further annular flange 323 extending fixedly and forwardly from the plate 320 in coaxial alignment with the through hole 324 in the plate 320.

The rearward annular flange 322 of the front cover 293 is fixedly secured within the cup 295 of the coupling 292 by any convenient means, for example by snap fit connectors on the opposing faces of such flange 322 and the peripheral wall 297 of the cup 295. For example, the cup peripheral wall 297 may be provided with several circumferentially spaced rectangular holes 325 (FIGS. 8A and 8B) for snap fit reception therein of small radially outward extending protrusions schematically indicated at 326 on the outside of the rearward annular flange 322.

The wand 294 further includes a relatively large diameter elongate suction tube 330 (FIGS. 8A and 8B) which loosely coaxially surrounds the irrigation liquid outlet tube 305 (FIG. 8) and extends substantially to the front end of the latter. The rear end portion 331 of the suction tube 330 is radially enlarged to provide a radially shallow, axially elongate flange protruding radially outward therefrom and which is axially trapped between the plate 320 and the gasket 321 backed by the base wall 296. This serves to rigidly fix the suction tube 330 with respect to the coupling 292 and front cover 293. A port 332 in the sidewall of the suction tube 330 near its rear end communicates with a loosely surrounding annular chamber 333 defined between the plate 320 and base wall 296 of the front cover 293 and coupling 292 respectively.

The front end of the irrigation liquid tube 305 is held coaxially fixed within the front end portion of the surrounding suction tube 330 by any convenient means, such as radial, circumferentially spaced, webs 334 (FIG. 8). Accordingly, with a tip unit 291, of the general type above described, installed on the front end of the handpiece, as shown in FIG. 8, irrigation liquid pulses from the pump 100 pass forwardly within the liquid tube 305 and are projected from the front (left in FIG. 8) end thereof, as schematically indicated by the arrows PL. At the same time, liquid and particulate debris at the surgical site SU are drawn into the front (left in FIG. 8) end of the suction tube 330, pass rearwardly along the length thereof, through the port 332 into the chamber 333 and rearwardly through the nipple 306 and suction nipple 285.

With the exception of a few components such as the motor 44, the various electrically conductive contacts, the elongate insulated conductors, the various seal rings (for example 105, 154, 304 and 310, the gasket 321, as well as the suction and irrigation liquid hoses, the remaining major components, while possibly manufacturable of a variety of materials, are economically manufacturable of available molded plastics materials. For example, the valve member 131 may be of rubber or a synthetic substitute or similar resilient plastic. Similarly, the bellows 101 is preferably molded of a suitable resilient plastic material capable of the bellows expansion and contraction movements shown in the drawings. The trigger unit 240 and the latch arm 312, while of substantially rigid plastics material, are elastically bendable to the extent required to suit the present description. Similarly, components to be snap-fitted together are substantially rigid but have sufficient resilience to permit the required described snap fitting.

The present invention can be constructed at relatively low cost and is thus practically manufacturable as a disposable tool, both the handpiece 10 itself and the accompanying electric power supply unit 190 being disposable after use with a single surgery patient.

OPERATION

The apparatus is quickly and easily assembled. The drive unit 25 (FIG. 12) is assembled by, in effect, "dropping in" elements in proper sequence into the right (lower in FIG. 12) shell 31 and covering same with the other shell 30. More particularly, output gear 60, face gear 54 and motor 36 (with attached pinion gear 53 and electric contacts 270 and 271) are "dropped" into their respective locations in the upturned shell part 31, in that sequence. The rectangular shaft 61, topped by the eccentric member 62, drops into the corresponding hole in the output gear 60 and the link member 51 drops onto the eccentric member. The other shell part 30 is then snap fitted over the filled shell part 31, completing the drive unit 25.

The pump unit 100 is assembled by coaxially telescoping together its elements shown in FIG. 18 and then plugging into the inlet port 146 (FIG. 19) the elbow 151 with the O-ring 154 and hose 160 assembled thereon.

The stub 120 (FIG. 18) of the drive unit 100 can then be snapped into the slot 122 of the drive unit fork 71 (FIG. 2) to connect the drive unit 25 operatively to the pump unit 100. The suction hose 280 can then be connected to the pump unit nipple 285 and to the nipple 282 on the clamp plate 165. Thereafter, the two assemblies above described can be laid into the rightward (FIG. 2) housing part 15 in the following order, namely liquid hose 160 (FIG. 4), drive unit 25 and pump unit 100 (FIG. 3) and, last, suction hose 280 and clamp plate 165.

The trigger unit 240 is then placed, with its rightward (FIG. 2) pivot stub 243 located in the corresponding boss 244 in the rightward housing part 15, and its arm 251 inserted through the hole 252 (FIG. 4A) into the interior of the handle portion of the rightward housing part 15, as seen in FIGS. 4 and 4A. The trigger arm 251 is "covered" by the rear portion 281 of the suction hose 280 in FIG. 3. The electrical contacts 262 and 263 are placed on their respective posts 255 and 256 in the rear portion of the rightward housing part 15 and the three forward electrical connectors 175 are secured respectively to the mentioned contacts 262 and 263 and the motor contact 271 (FIG. 4A). Thereafter, the leftward (FIG. 2) housing part 14 can be snap fitted to the rightward housing part 15 to close same and enclose the above mentioned apparatus, shown in FIG. 3, therein.

In the thus assembled handpiece, the drive unit is fixedly located by engagement of its drive axis bosses 84 and 85 (FIG. 5) in corresponding bosses in the housing parts 14 and 15 (see for example at 96 in housing part 15 in FIG. 2). Location of the drive unit 25 is assisted by the ribs 95 within the housing parts 14 and 15 and by snug resilient engagement of the drive unit 25 by the hoses 160 and 280 which flank it.

The drive unit shell 26 is configured to maintain the proper tolerances between meshing gears and related parts. Location of all the drive unit parts in the drive unit shell 26 reduces the need to maintain close tolerances in the larger and less specialized handle housing 11. Even the housing tolerances, for locating the pump unit 100 with respect to the drive unit 25 in the housing 11, need not be close since the bellows 101 are flexible enough to bend or otherwise distort to absorb minor mis-alignment or angulation of the reciprocation axis of the link member 51 with respect to the length axis of the pump unit 100. Indeed, the ribs 95 in the housing 11 permit pivoting of the drive unit 25 about the axis of the bosses 96 to allow the drive unit 25 and pump unit 100 to settle into their own working relative orientation. Accordingly, the precision in the handpiece housing 11 can be concentrated in aspects of fitting together of the two housing halves.

The electric power supply unit 190 (FIG. 22) is quickly and easily assembled. More particularly, the feet of the respective battery contacts 210, 211, 212 (FIGS. 26–28) are slid downward into their respective grooves (FIGS. 23A and 23B) in the pan 192 (FIG. 22) with their protruding toes resiliently gripping the sides of the grooves. The rear connectors 176 are connected to the battery contact fingers 224 and 225 in the order shown in FIG. 22A. The batteries B1–B8 are then slipped down into the pan in the orientation shown in FIG. 22 and into electrically conductive engagement with the battery contacts 210, 211 and 212 indicated in FIG. 22A. The rear portion of the liquid hose 160 is laid atop the batteries as indicated in FIG. 23, with the square flange 182 nonrotatable in the boss 235, and the cover 193 is snap fitted atop the liquid hose 160 and battery filled pan 192, as shown in FIG. 23, to complete assembly of the power supply unit. The cap 185 is pressed onto the sharpened tip 184 to protect it prior to use.

The result is a disposable pulsed irrigation handpiece unit which is entirely self-contained, including its own power supply, and which is ready for use upon having its sharpened tip 184 plugged into a conventional irrigation liquid supply bag or the like, and a conventional manner.

It should be noted that virtually the entire handpiece 10 and power supply unit 190 can be assembled without need for any adhesives, the parts going together with friction or snap fits or, in the case of the joinder of the bellows housing 104 to the bellows 100 and elbow 151, by being held together by surrounding structure which in turn is snap fitted together. This greatly eases and speeds assembly. A minor exception is that the fitting 180 is here adhesively fixed to the hose 160.

To use the handpiece assembly in surgery, the cap 185 (FIG. 23) is removed from the pointed tip 183, which is then plugged into a standard output fitting on a conventional irrigation liquid supply bag. The power supply unit 190, being fixed to the rear end of the irrigation liquid hose 160, can be allowed to simply hang from the irrigation liquid supply bag (not shown but schematically indicated at S in FIG. 22). By providing a substantial length of irrigation liquid hose 160 (for example 10 feet), the liquid supply bag S and power supply unit 190 can be located well out of the way of the surgical team during use of the handpiece 10 at the surgical site. Even then, the power supply unit 190 is compact as compared to the adjacent conventional irrigational liquid supply bag (being very little larger than the eight conventional double AA batteries that it houses).

If suction will be desired at the surgical site, the handpiece nipple 283 (FIG. 3) can be connected by a conventional hose not shown to a conventional suction source SS (FIG. 3).

A variety of tip units 291 of differing characteristics (e.g. differing irrigation liquid spray patterns, etc.) may be made available for alternative mounting on the handpiece 10. One example is shown in FIGS. 8, 8A and 8B.

In any event, the user selects a tip unit 291 having a wand 294 of desired configuration, and rearwardly inserts its coupling 292 into the front end of the handpiece 11. More particularly, the nipples 301 and 306 of the tip unit are inserted coaxially rearwardly, in sealed relation (see FIG. 8) in the conduits 143 and 286 respectively of the bellows housing 104. The resilient latch arm 312 enters the barrel 13 of the handpiece housing 11 adjacent to the bellows housing 104 until the plate 320 of the front cover 293 abuts the front end of the handpiece housing barrel 13. In the last part of this tip installation movement, the wedge shaped ridge 313 (FIG. 8) on the latch arm 312 snaps past the rib 314 of the housing barrel 13 to positively prevent forward removal of the tip unit from the handpiece.

To use the apparatus for irrigation of a surgical site, the user grips the handpiece, either by the handle 12, in a pistol-like manner, or where the barrel 13 joins the handle 12, in a wand like manner. In either position, the user has one or more fingers that can bear on and press inwardly the trigger lever 242 from its inoperative rest position shown in solid line in FIG. 4A forward and through its low speed and high speed positions indicated in broken lines at 253B and 253C in FIG. 4A. In the first operative position 253B, the blade 253 connects the low speed (here six-volt) contact 266 to the motor contact 270. On the other hand, in the fully depressed condition of the trigger, indicated at 253C, the blade 253 connects the high speed, 12 volt contact 267 with the motor contact 270. Accordingly, the user can select between "off", lower power pulsing and high power pulsing.

In one embodiment pump stroke was about ¼". In one embodiment shown, the motor speed was about 15,000 rpm and the speed reduction afforded by the transmission was about 15-1, providing the eccentric with about 1,000 rpm speed.

Depending on the flow resistance of the particular tip unit attached to the handpiece, the liquid pulse frequency may change. In one example, a handpiece according to the invention produced about 1200 pulses per minute, dispensing about 1600 ml per minute of irrigation liquid in about 1.3 ml liquid pulses. The positive drive of the pump unit by the drive unit and the location of the pump unit, near the front end of the barrel 13 and in direct engagement with the tip unit, provides liquid pulses at the output of the tip unit which have sharp rise and fall slopes. Thus, the relationship of liquid pulse amplitude to time approximates a square wave form, more so than for example, the aforementioned device of U.S. Pat. No. 5,046,486. Further, the force applied to the pulses by the present apparatus is higher (somewhat above one Newton) than in that prior art device, at the full power position of the trigger.

In one embodiment according to the invention, a tab 316 (FIGS. 1 and 8B) extends forward from the front plate 320 of the front cover 293, on the opposite side of the wand 294 from the latch arm 312. To release the latch arm 312 from the housing 11, the user can thus simply simultaneously grip with opposite fingers and pinch toward each other the latch arm 312 and tab 316. In other words the tab 316 provides base toward which to pinch, or pull, the latch arm 312 to release the tip unit 291 from the handpiece 11.

In the present invention, the liquid and suction nipples of the tip unit connect directly to the pump unit 100, and do not contact any part of the handpiece housing 11. Accordingly, neither the pump unit 100 nor tip unit 291 need fit with close tolerances the handpiece housing 11. The connection of the tip unit to the handpiece housing is merely to latch the tip unit against loss from the handpiece housing and to casually cover the open front end of the handpiece housing. Accordingly, the liquid tight fit is between the nipples of the tip unit and conduits of the pump unit, not with the housing.

Although a particular preferred embodiment of the invention has been disclosed in detail for illustrative purposes, it will be recognized that variations or modifications of the disclosed apparatus, including the rearrangement of parts, lie within the scope of the present invention.

The invention claimed is:

1. A medical irrigator comprising:
   a housing shaped to be hand held and having a front end;
   an inlet tube extending to said housing;
   a pulse pump capable of operating at a variable rate disposed in said housing and having an outlet conduit that opens to the housing front end, said pump configured to receive fluid from said inlet tube and discharging the fluid through said outlet conduit;
   a single electric motor disposed in said housing and connected to said pump for actuating said pump, said motor operable at variable speeds to control the pumping rate of said pump;
   a control assembly disposed in said housing to regulate the speed of said motor;
   a suction tube disposed in said housing that has an open end adjacent the front end of said housing that extends away from the front end;
   a battery pack separate from said housing; and
   a flexible conductor assembly extending from said battery pack to said housing for supplying energy stored in said battery pack to said motor.

2. The medical irrigator of claim 1, wherein said control assembly has a switch that is moveably mounted to said housing, said control assembly configured so that:
   when said switch is in a first position, said control assembly does not supply an energization signal to said motor;
   when said switch is in a second position, said control assembly supplies a first energization signal from said battery pack to said motor; and
   when said switch is in a third position, said control assembly supplies a second energization signal from said battery pack to said motor.

3. The medical irrigator of claim 2, wherein said switch is pivotally attached to said housing.

4. The medical irrigator of claim 3, wherein said switch is configured to move:
   from the first position and to the second position; and
   from the second position to the third position.

5. The medical irrigator of claim 2, wherein said switch is configured to move:
   from the first position and to the second position; and
   from the second position to the third position.

6. The medical irrigator of claim 1, wherein said pump is bellows pump.

7. The medical irrigator of claim 1, wherein said housing is formed to have: a handle; and a barrel integral with and located above said handle that extends forward from said handle, said barrel having the housing front end from which said pump discharges fluid and from which said suction tube extends.

8. The medical irrigator of claim 1, wherein said pump is a reciprocating pump.

9. The medical irrigator of claim 1, wherein said inlet tube extends from said battery pack to said housing.

10. A medical irrigator having:
    a housing shaped to be hand held, said housing having a front face shaped to receive a medical/surgical tip assembly;
    a discharge conduit disposed in said housing that opens into the front face of said housing and a suction tube that extends from the housing front face, both said discharge conduit and said suction tube being configured to be connected to separate conduits integral with the tip assembly;
    an inlet line connected to said housing;
    a pump disposed in said housing connected to receive fluid from said inlet line and pump fluid out through said discharge conduit, said pump being a pulse pump that operates at a variable rate;
    a single, variable speed electric motor in said housing that is connected to said pump that actuates said pump so as to regulate the pumping rate of said pump;
    a conductor assembly including a plurality of flexible conductors, said conductor assembly having a distal end disposed in said housing and a proximal end spaced from said housing;
    a battery pack separate from said housing, said battery pack attached to said conductors at the proximal end of said conductor assembly; and
    a switch assembly mounted to said housing for selectively establishing a connection between at least one of said conductors and said motor, said switch assembly having a switch element moveably attached to said handle, said switch assembly being configured so that:

when said switch element is in a first position, said switch assembly does not supply an energization signal to said motor;

when said switch element is in a second position, said switch assembly supplies a first energization signal from said battery pack to said motor; and when said switch element is in a third position, said switch assembly supplies a second energization signal from said battery pack to said motor.

11. The medical irrigator of claim 10, wherein said switch element is pivotally attached to said housing.

12. The medical irrigator of claim 10, wherein said switch element is configured to move:
from the first position and to the second position; and
from the second position to the third position.

13. The medical irrigator of claim 10, wherein:
said conductor assembly includes: a first conductor over which a first energization signal from said battery pack is supplied; and a second conductor over which a second energization signal from said battery pack is supplied; and
said switch assembly is configured so that:
when said switch element is in the second position, said switch assembly connects said first conductor to said motor; and
when said switch element is in the third position. said switch assembly connects said second conductor to said motor.

14. The medical irrigator of claim 10, wherein said switch assembly includes a single conductive member that is directly connected to said motor.

15. The medical irrigator of claim 10, wherein said pump is a bellows pump.

16. The medical irrigator of claim 10, wherein said switch element is pivotally attached to said housing.

17. The medical irrigator of claim 10, wherein said pump is a reciprocating pump.

18. The medical irrigator of claim 10, wherein said inlet tube extends from said battery pack to said housing.

19. The medical irrigator of claim 10, wherein:
said inlet line is a flexible hose that extends from outside said housing into said housing; and
said conductor assembly is attached to said hose so that at least a portion of said conductor assembly extends along said hose.

20. A medical irrigator comprising:
a housing shaped to have a front end;
a suction tube disposed in said housing having an inlet end that opens from the front end of said housing;
a pulse discharge pump that operates at a variable rate disposed in said housing having an inlet and discharge conduit, the discharge conduit opening towards the front end of said housing;
an inlet line that extends into said housing that is in fluid communication with the pump inlet;
a single electric motor disposed in said housing and connected to said pump to actuate said pump, said motor operating at variable speeds to regulate the pumping rate of said pump;
a battery pack separate and spaced from said housing that contains at least one battery that stores energy for energizing said motor;
a flexible cable that extends from said battery pack to said housing for supplying energy from said battery pack to said motor; and
a control assembly integral with said housing, said control assembly having a switch member moveably mounted to said housing and said control assembly being configured to apply a variable energization signal from said battery pack to said motor so as to control the speed of said motor and regulate the pumping rate of said pump.

21. The medical irrigator of claim 20, wherein said control assembly is configured so that said switch member moves sequentially from a first position to a second position and from the second position to a third position and:
when said switch member is in the first position, the switch member does not establish a connection between said cable and said motor;
when said switch member is in the second position, the switch member establishes a connection between said cable and said motor to cause a first energization signal to be applied to said motor; and
when said switch member is in the third position, the switch member establishes a connection between said cable and said motor to cause a second energization signal to be applied to said motor.

22. The medical irrigator of claim 20, wherein:
said cable includes a first conductor over which a first energization signal is available from said battery pack and a second conductor over which a second energization signal is available from said battery pack; and
said control assembly is configured so that switch member can be selectively positioned to: connect neither of said cable conductors to said motor; connect the first said cable conductor to said motor; or connect the second said cable conductor to said motor.

23. The medical irrigator of claim 22, wherein said control assembly is configured to sequentially move from the position in which neither said cable conductors are connected to said motor to the position in which said first cable conductor is connected to said motor and to the position in which the second said cable conductor is connected to said motor.

24. The medical irrigator of claim 20, wherein said pump is a reciprocating pump.

25. The medical irrigator of claim 20, wherein said pump is a bellows pump.

26. The medical irrigator of claim 20, wherein said inlet line extends from said battery pack to said housing.

27. The medical irrigator of claim 20, wherein:
said inlet line is a flexible hose that extends from outside said housing into said housing; and
said cable is attached to said hose so that at least a portion of said cable extends along said hose.

28. A medical irrigator, said irrigator comprising:
a housing having a front face shaped to receive a medical tip assembly;
a pulse discharge pump that operates a variable rate, said pump having an inlet and an outlet, the outlet opening into the front face of said housing so as to be in fluid communication with a first conduit of the tip assembly;
a suction tube in said housing having an open end located adjacent the front face of said barrel so as to be in fluid communication with a second conduit of the tip assembly;
a single, variable speed electrical motor disposed in said housing connected to said pump for actuating said pump at variable rates;
a battery unit separate from said housing for supplying energy to said motor;
a control assembly mounted to said housing and connected to said battery unit and to said motor for supplying a variable potential energization signal to said motor, said control assembly having a single switch member that is moveably attached to said housing that selectively makes/breaks a connection between said battery unit and said motor and establishes the potential of the energization signal supplied to said motor.

29. The medical irrigator of claim 28, wherein said control assembly is configured so that said switch member moves sequentially from a first position to a second position and from the second position to a third position and:
when said switch member is in the first position, the switch member does not establish a connection between said battery unit and said motor;
when said switch member is in the second position, the switch member establishes a connection between said battery unit and said motor to cause a first energization signal to be applied to said motor; and
when said switch member is in the third position, the switch member establishes a connection between said battery unit and said motor to cause a second energization signal to be applied to said motor.

30. The medical irrigator of claim 28, wherein said control assembly has a first contact over which a first energization signal is available from said battery unit and a second contact over which a second energization signal is available from said battery unit and said control assembly is configured so that said switch member can be selectively positioned to: connect neither of said contacts to said motor; connect the first said contact to said motor; or connect the second said contact to said motor.

31. The medical irrigator of claim 30, wherein said control assembly contacts are statically mounted to said housing.

32. The medical irrigator of claim 30, wherein said control assembly is configured so that said switch member moves sequentially from:
a position in which no energization signal-supply contacts are connected to said motor to a position in which said first contact is connected to said motor; and
from the position in which said first contact is connected to said motor to a position in which said second contact is connected to said motor.

33. The medical irrigator of claim 28, wherein said pump is a reciprocating pump.

34. The medical irrigator of claim 28, wherein said pump is a bellows pump.

35. The medical irrigator of claim 28, wherein a flexible cable extends from said battery unit to said control assembly.

36. The medical irrigator of claim 28, wherein said housing includes a handle and a barrel that extends above and projects forward of said handle, said barrel having the front face of said housing.

37. The medical irrigator of claim 28, wherein:
a flexible hose extends from outside said housing into said housing through which fluid is supplied to the pump inlet; and
a flexible cable extends from said battery unit to said housing, said cable being connected to said control assembly and being attached to said hose so that at least a portion of said cable extends along said hose.

38. A medical irrigator, said irrigator comprising:
a housing having a front face shaped to receive a medical tip assembly;
a pulse discharge pump disposed in said housing that operates at a variable rate, said pump having an inlet and an outlet, the outlet opening into the front face of said housing so as to be in fluid communication with a first conduit of the tip assembly;
a suction tube in said housing having an open end located adjacent the front face of said housing so as to be in fluid communication with a second conduit of the tip assembly;
a single, variable speed electric motor disposed in said housing connected to said pump for actuating said pump at variable rates;
a battery pack separate from said housing containing at least one battery;
a flexible cable that extends from said battery pack to said housing, said flexible cable having at least one conductor over which an energization signal from said at least one battery is supplied; and
a control assembly attached to said housing and connected between said at least one conductor and said motor for supplying a variable potential energization signal to said motor, said control assembly having a single switch member that is moveably attached to said housing that selectively makes/breaks a connection between said at least one conductor and said motor and that establishes the potential of the energization signal supplied to said motor.

39. The medical irrigator of claim 38, wherein said control assembly is configured so that said switch member moves sequentially from a first position to a second position and from the second position to a third position and:
when said switch member is in the first position, the switch member does not establish a connection between said at least one conductor and said motor;
when said switch member is in the second position, the switch member establishes a connection between said at least one conductor and said motor to cause a first energization signal to be applied to said motor; and
when said switch member is in the third position, the switch member establishes a connection between said at least one conductor and said motor to cause a second energization signal to be applied to said motor.

40. The medical irrigator of claim 38, wherein:
said cable has a first conductor over which a first energization signal is available from said at least one battery and a second conductor over which a second energization signal is available from said at least one battery; and
said control assembly is configured so that switch member can be selectively positioned to: connect neither of said cable conductors to said motor; connect the first said cable conductor to said motor; or connect the second said cable conductor to said motor.

41. The medical irrigator of claim 40, wherein said control assembly has a first contact to which said first cable conductor is attached and a second contact to which said second cable conductor is attached and said contacts are statically mounted to said housing.

42. The medical irrigator of claim 40, wherein said control assembly is configured so that said switch element moves sequentially from:
a position in which no energization signal-supplying conductors are connected to said motor to a position in which said first cable conductor is connected to said motor; and
from the position in which said first cable conductor is connected to said motor to a position in which said second cable conductor is connected to said motor.

43. The medical irrigator of claim 38, wherein an inlet hose extends from said battery pack to said housing, said inlet hose being connected to the pump inlet.

44. The medical irrigator of claim 38, wherein said housing is shaped to have a handle and a barrel integral with said handle that is located above and projects forward of said handle.

45. The medical irrigator of claim 44, wherein said motor is disposed in said housing handle.

46. The medical irrigator of claim 38, wherein:

a flexible hose extends from outside said housing into said housing through which fluid is supplied to the pump inlet; and said cable is attached to said hose so that at least a portion of said cable assembly extends along said hose.

* * * * *